(12) United States Patent
Oda et al.

(10) Patent No.: US 8,033,824 B2
(45) Date of Patent: Oct. 11, 2011

(54) SELF-LIGATING ORTHODONTIC BRACKET AND DEVICES FOR DEPLOYING SAME

(75) Inventors: Todd I. Oda, Torrance, CA (US);
Farrokh Farzin-Nia, Inglewood, CA (US); Jefferson Sabilla, Ontario, CA (US); Hamid Sheikh, Chino, CA (US); Dwight Damon, Spokane, WA (US)

(73) Assignee: Ormco Corporation, Orange, CA (US)

( * ) Notice: Subject to any disclaimer, the term of this patent is extended or adjusted under 35 U.S.C. 154(b) by 406 days.

(21) Appl. No.: 12/147,877

(22) Filed: Jun. 27, 2008

(65) Prior Publication Data

US 2009/0004619 A1    Jan. 1, 2009

Related U.S. Application Data

(60) Provisional application No. 60/946,842, filed on Jun. 28, 2007, provisional application No. 61/022,570, filed on Jan. 22, 2008.

(51) Int. Cl.
*A61C 3/00* (2006.01)
(52) U.S. Cl. ............................................. 433/11; 433/10
(58) Field of Classification Search .................... 433/10, 433/11
See application file for complete search history.

(56) References Cited

U.S. PATENT DOCUMENTS

| | | | |
|---|---|---|---|
| 2,549,528 A | 4/1951 | Russell | |
| 2,671,964 A | 3/1954 | Russell et al. | |
| 2,686,365 A | 8/1954 | Schurter | |
| 3,087,244 A | 4/1963 | Huettner et al. | |
| 3,438,132 A | 4/1969 | Rubin | |
| 3,748,740 A | 7/1973 | Wildman | |
| 3,750,288 A | 8/1973 | Culbreth | |
| 3,772,787 A | 11/1973 | Hanson | |
| 3,780,437 A | 12/1973 | Wildman | |
| 3,946,488 A | 3/1976 | Miller et al. | |
| RE28,889 E | 7/1976 | Wildman | |
| 4,077,126 A | 3/1978 | Pletcher | |
| 4,144,642 A | 3/1979 | Wallshein | |
| 4,209,906 A | 7/1980 | Fujita | |
| 4,248,588 A | 2/1981 | Hanson | |
| 4,355,975 A | 10/1982 | Fujita | |

(Continued)

FOREIGN PATENT DOCUMENTS

EP    0 623 320    11/1994

(Continued)

OTHER PUBLICATIONS

Roche, Olivier (Authorized Officer); International Search Report and Written Opinion; Jan. 12, 2009; 17 pages; European Patent Office.

(Continued)

*Primary Examiner* — Ralph Lewis
(74) *Attorney, Agent, or Firm* — Wood, Herron & Evans, L.L.P.

(57) ABSTRACT

An orthodontic bracket for coupling an archwire with a tooth includes a bracket body having an archwire slot adapted to receive the archwire therein and a movable member engaged with the bracket body and movable between an opened position and a closed position. A securing mechanism is configured to secure the movable member in at least the closed position and includes a projecting portion and a receiving portion. The projecting portion may include a generally elongate pin capable of flexing relative to a central axis thereof to secure the movable member in at least the closed position. An orthodontic assembly includes an orthodontic bracket and an alignment device for positioning the bracket on the tooth.

23 Claims, 14 Drawing Sheets

U.S. PATENT DOCUMENTS

| | | |
|---|---|---|
| 4,371,337 A | 2/1983 | Pletcher |
| 4,419,078 A | 12/1983 | Pletcher |
| 4,559,012 A | 12/1985 | Pletcher |
| 4,655,708 A | 4/1987 | Fujita |
| 4,799,882 A | 1/1989 | Kesling |
| 4,878,840 A | 11/1989 | Reynolds |
| 5,094,614 A | 3/1992 | Wildman |
| 5,269,681 A | 12/1993 | Degnan |
| 5,275,557 A | 1/1994 | Damon |
| 5,295,886 A | 3/1994 | Wildman |
| 5,322,435 A | 6/1994 | Pletcher |
| 5,429,500 A | 7/1995 | Damon |
| 5,439,378 A | 8/1995 | Damon |
| 5,466,151 A | 11/1995 | Damon |
| 5,474,444 A | 12/1995 | Wildman |
| 5,474,445 A | 12/1995 | Voudouris |
| 5,474,446 A | 12/1995 | Wildman et al. |
| 5,511,976 A | 4/1996 | Wildman |
| 5,630,715 A | 5/1997 | Voudouris |
| 5,630,716 A | 5/1997 | Hanson |
| 5,791,897 A | 8/1998 | Wildman |
| 5,857,849 A | 1/1999 | Kurz |
| 5,857,850 A | 1/1999 | Voudouris |
| 5,863,198 A | 1/1999 | Doyle |
| 5,863,199 A | 1/1999 | Wildman |
| 5,873,716 A | 2/1999 | Kesling |
| 5,890,893 A | 4/1999 | Heiser |
| 5,906,486 A | 5/1999 | Hanson |
| 5,908,293 A | 6/1999 | Voudouris |
| 5,913,680 A | 6/1999 | Voudouris |
| 5,971,753 A | 10/1999 | Heiser |
| 6,071,118 A | 6/2000 | Damon |
| 6,071,119 A | 6/2000 | Christoff et al. |
| 6,168,428 B1 | 1/2001 | Voudouris |
| 6,190,166 B1 | 2/2001 | Sasakura |
| 6,193,508 B1 | 2/2001 | Georgakis |
| 6,247,923 B1 | 6/2001 | Vashi |
| 6,368,105 B1 | 4/2002 | Voudouris et al. |
| 6,428,314 B1 | 8/2002 | Jones, Jr. et al. |
| 6,485,299 B1 | 11/2002 | Wildman |
| 6,632,088 B2 | 10/2003 | Voudouris |
| 6,726,474 B2 | 4/2004 | Spencer |
| 7,267,545 B2 | 9/2007 | Oda |
| 7,416,408 B2 | 8/2008 | Farzin-Nia et al. |
| 7,621,743 B2 | 11/2009 | Bathen et al. |
| 2002/0006595 A1 | 1/2002 | Voudouris |
| 2005/0239012 A1 | 10/2005 | Bathen |
| 2005/0244775 A1 | 11/2005 | Abels et al. |
| 2005/0277082 A1 | 12/2005 | Christoff |
| 2006/0177790 A1 | 8/2006 | Farzin-Nia et al. |
| 2006/0228662 A1 | 10/2006 | Lokar et al. |
| 2006/0263737 A1 | 11/2006 | Oda |
| 2007/0072143 A1 | 3/2007 | Sommer |
| 2007/0082315 A1 | 4/2007 | Sabater |
| 2007/0160949 A1 | 7/2007 | Voudouris |
| 2007/0178422 A1 | 8/2007 | Voudouris |
| 2007/0224569 A1 | 9/2007 | Oda |
| 2007/0243497 A1 | 10/2007 | Voudouris |
| 2007/0248928 A1 | 10/2007 | Damon |
| 2007/0259301 A1 | 11/2007 | Hagelganz et al. |
| 2007/0259304 A1 | 11/2007 | Hagelganz et al. |
| 2008/0113311 A1 | 5/2008 | Forster |
| 2009/0155734 A1 | 6/2009 | Damon |
| 2010/0178629 A1 | 7/2010 | Oda et al. |
| 2010/0196838 A1 | 8/2010 | Damon |

FOREIGN PATENT DOCUMENTS

| | | |
|---|---|---|
| EP | 1 508 310 | 2/2005 |
| WO | 94/23666 | 10/1994 |

OTHER PUBLICATIONS http://www.classoneorthodontics.com, website, Feb. 9, 2009, 3 pgs.

U.S. Patent and Trademark Office, International Search Report and Written Opinion in PCT Application No. PCT/US2010/023718, Apr. 15, 2010.

U.S. Patent and Trademark Office, International Search Report and Written Opinion in PCT Application No. PCT/US2010/021153, Mar. 22, 2010.

Radial. (n.d.) Dictionary.com Unabridged. Retrieved Oct. 20, 2009, from Dictionary.com website: http://dictionary.reference.com/browse/radial.

European Patent Office, International Preliminary Report on Patentability in PCT Application No. PCT/US2008/068545, Jan. 5, 2010.

SELF-LIGATING ORTHODONTIC BRACKET AND DEVICES FOR DEPLOYING SAME

CROSS REFERENCE TO RELATED CASES

This application claims priority to U.S. Provisional Patent Application Ser. No. 60/946,842 filed Jun. 28, 2007; and U.S. Provisional Patent Application Ser. No. 61/022,570 filed Jan. 22, 2008, the disclosures of each being incorporated by reference herein in their entirety.

TECHNICAL FIELD

The invention relates generally to orthodontic brackets and, more particularly, to self-ligating orthodontic brackets having movable closure members such as slides or latches and related tools for deploying the same.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While self-ligating brackets have been generally successful, manufacturers of such brackets continually strive to improve the aesthetics associated with self-ligating brackets, the use and functionality of self-ligating brackets, and the costs and manufacturability of self-ligating brackets.

SUMMARY

To these ends, an orthodontic bracket for coupling an archwire with a tooth includes a bracket body configured to be mounted to the tooth and having an archwire slot adapted to receive the archwire therein. A movable member is engaged with the bracket body and movable relative thereto between an opened position in which the archwire is insertable into the archwire slot, and a closed position in which the movable member retains the archwire in the archwire slot. A securing mechanism is configured to secure the movable member in at least the closed position and includes a projecting portion in one of the bracket body or movable member, and a receiving portion in the other of the bracket body or movable member. The projecting portion may include a generally elongate pin capable of flexing relative to a central axis thereof and cooperating with the receiving portion to secure the movable member in at least the closed position.

In one embodiment, the elongate pin is flexible in a generally radial direction relative to the central axis. By way of example, the elongate pin may be tubular and/or may include a slot that extends for at least a portion of a length of the pin so as to facilitate a radial expansion and contraction of the pin. In another embodiment, the elongate pin may be solid and may be flexible in a generally lateral direction relative to the central axis. In one embodiment, the projecting portion may be associated with the bracket body and the receiving portion associated with the movable member, which may be, for example, a ligating slide.

In one embodiment, the receiving portion includes a retaining slot adapted to receive the projecting member, such as the elongate pin. The retaining slot may include a first enlarged portion at a first end of the retaining slot having a first cross dimension. A straight segment portion is in communication with the first enlarged portion and includes a second cross dimension less than the first cross dimension to define at least one protrusion at the transition therebetween. The at least one protrusion provides resistance to movement of the movable member away from the closed position. The retaining slot may further include a second enlarged portion at a second end thereof. The second enlarged portion is in communication with the straight segment portion and has a third cross dimension that is larger than the second cross dimension of the straight segment portion to define at least one protrusion at the transition therebetween. This at least one protrusion provides resistance to movement of the movable member away from the opened position. The straight segment portion may be tapered so as to vary the sliding force for moving the movable member between the opened and closed positions. In another embodiment, the retaining slot may include at least one offset portion at an end thereof defining a first centerline, and a straight segment portion communicating with the offset portion and defining a second centerline spaced from the first centerline to define at least one protrusion at the transition therebetween.

In various embodiments, the movable member may include a pushing element adjacent an end thereof for guiding the archwire into the archwire slot as the movable member is moved toward the closed position. The pushing element may include a chamfer formed adjacent a leading edge of the movable member. The chamfer may be uniform across the width of the movable member or may be non-uniform, such as being adjacent the side edges of the movable member and away from its central region. Additionally, in some embodiments, the projecting portion may be oriented so as to be substantially perpendicular to the archwire slot of the bracket. In other embodiments, however, the projecting portion may be oriented so as to be substantially parallel to the archwire slot. Furthermore, in addition to securing the movable member in at least the closed position (and possibly the opened position), the securing mechanism may be further configured to prevent the movable member from disengaging the bracket body. For example, the elongate pin may engage a first end of the retaining slot when the movable member is in the opened position to thereby prevent the movable member from disengaging the bracket body.

In another embodiment, an orthodontic bracket for coupling an archwire with a tooth includes a bracket body configured to be mounted to the tooth and having an archwire slot adapted to receive the archwire therein. A movable member is engaged with the bracket body and movable relative thereto between an opened position and a closed position. A securing mechanism is configured to secure the movable member in at least the closed position and includes a projecting portion in one of the bracket body or movable member and a receiving portion in the other of the bracket body or movable member. At least a portion of the projecting portion is capable of moving between an expanded state and a contracted state, the projecting portion defining a first cross dimension in the expanded state and a second cross dimension less than the first cross dimension in the contracted state.

In still another embodiment, an orthodontic bracket for coupling an archwire with a tooth includes a bracket body configured to be mounted to the tooth and having an archwire slot for receiving the archwire therein. The bracket body further includes a confronting side adapted to confront teeth on an opposing jaw when mounted to the tooth. The confronting side includes a contoured shape so as to prevent occlusal interference with teeth on the opposing jaw. A cutout is formed in the confronting side of the bracket body and adapted to receive a connecting member for coupling the bracket to orthodontic devices on adjacent teeth. The cutout includes at least one bounding surface that limits movement of the connecting member in a direction generally perpendicular to the archwire slot and away from the tooth on which the bracket is mounted. The bracket may be a molar bracket and/or a self-ligating bracket and lack conventional tie wings.

In yet another embodiment, an orthodontic bracket for coupling an archwire with a tooth includes a bracket body configured to be mounted to a tooth and having an archwire slot for receiving the archwire therein. A movable member is engaged with the bracket body and movable relative thereto between an opened position and a closed position. The bracket includes a smooth generally arcuate outer surface adapted to confront and engage tissue in the oral cavity (e.g., cheek tissue). In one embodiment, the movable member includes an outer contoured portion that forms a substantial portion of the arcuate surface of the bracket. The arcuate surface may be characterized by one or more relatively large radii of curvature in, for example, a gingival-occlusal direction and/or a mesial-distal direction.

In still another embodiment, an orthodontic bracket includes a bracket body configured to be mounted to a tooth and having an archwire slot adapted to receive an archwire therein. A movable member is engaged with the bracket body and movable relative thereto between an opened position and a closed position. A first slot is formed in the bracket body and adapted to receive a first orthodontic device. The first slot may extend in a direction generally parallel to the archwire slot. The bracket body may further include a second slot adapted to receive a second orthodontic device, the second slot extending in a direction generally perpendicular to the archwire slot. In one embodiment, the first and second slots do not intersect one another.

A method for moving a tooth to effect orthodontic treatment using an orthodontic bracket, wherein the orthodontic bracket includes a bracket body configured to be mounted to a tooth, an archwire slot adapted to receive an archwire therein, and a slot formed in the bracket body and extending in a direction generally parallel to the archwire slot, includes mounting the bracket to a tooth and coupling a temporary attachment device to the bracket using the slot. In one embodiment, the tooth may be coupled to a jaw bone of a patient and the method may further include anchoring a temporary anchoring device to the jaw bone to establish a fixed spacial point, and coupling the temporary anchoring device to the bracket using the slot so as to move the tooth relative to the fixed spacial point.

In yet a further embodiment, an orthodontic assembly includes an orthodontic bracket for coupling an archwire to a tooth, the bracket including an archwire slot for receiving the archwire therein and a bonding surface adapted to be coupled to the tooth, and alignment device releasably coupled to the orthodontic bracket and configured for deploying the orthodontic bracket onto the tooth. The alignment device includes a first portion adapted to releasably coupled to the orthodontic bracket and a second portion offset from the first portion and adapted to be adjacent a surface of the tooth when the bonding surface of the bracket is positioned on the surface of the tooth. The second portion may include a plurality of markers to facilitate positioning of the bracket on the tooth, such as by using a fixed reference point on the tooth. The coupled orthodontic bracket and alignment device may be pre-packaged for delivery to a doctor's office. In this way, the problems associated with field assembly may be avoided. Additionally, the alignment device may be disposable.

In one embodiment, the alignment device includes a first coupling feature and the orthodontic bracket includes a second coupling feature that cooperates with the first coupling feature to restrict movement of the orthodontic bracket relative to the alignment device in a direction generally parallel to the archwire slot. For example, the first coupling feature may include a projecting tab on the alignment device and the second coupling feature may include a recess in the bracket body. The recess may be, for example, a tool receptacle used for opening a self-ligating orthodontic bracket with an opening tool.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Although the invention will be described in connection with certain embodiments, the invention is not limited to practice in any one specific type of self-ligating orthodontic bracket. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

Figure 1:
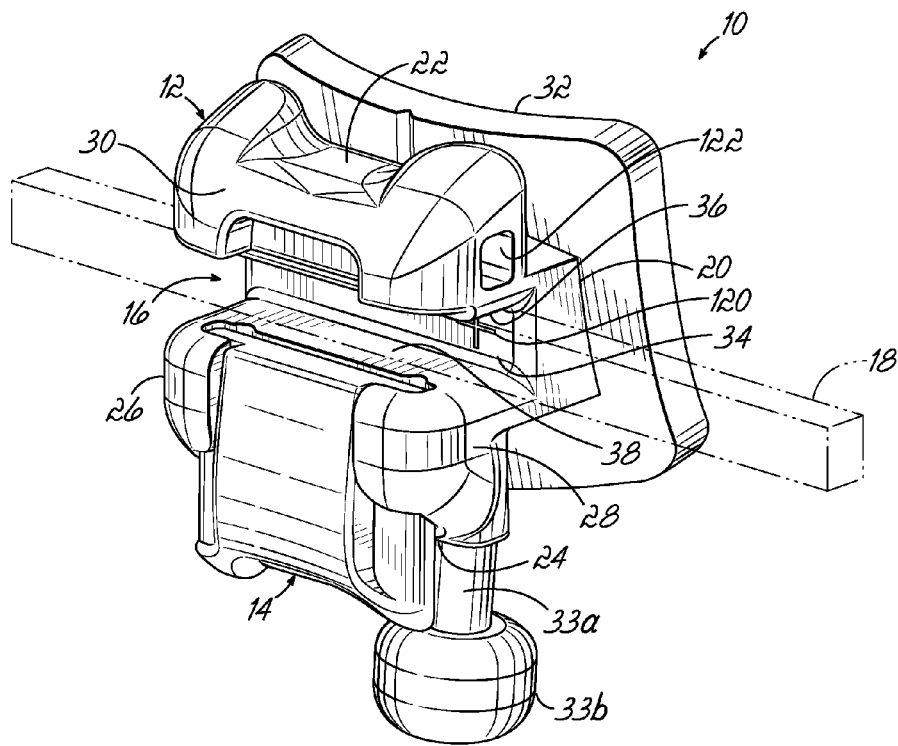
FIG. 1 is a perspective view of a self-ligating orthodontic bracket in accordance with one embodiment of the invention, the ligating slide shown in the opened position.
Figure 2:
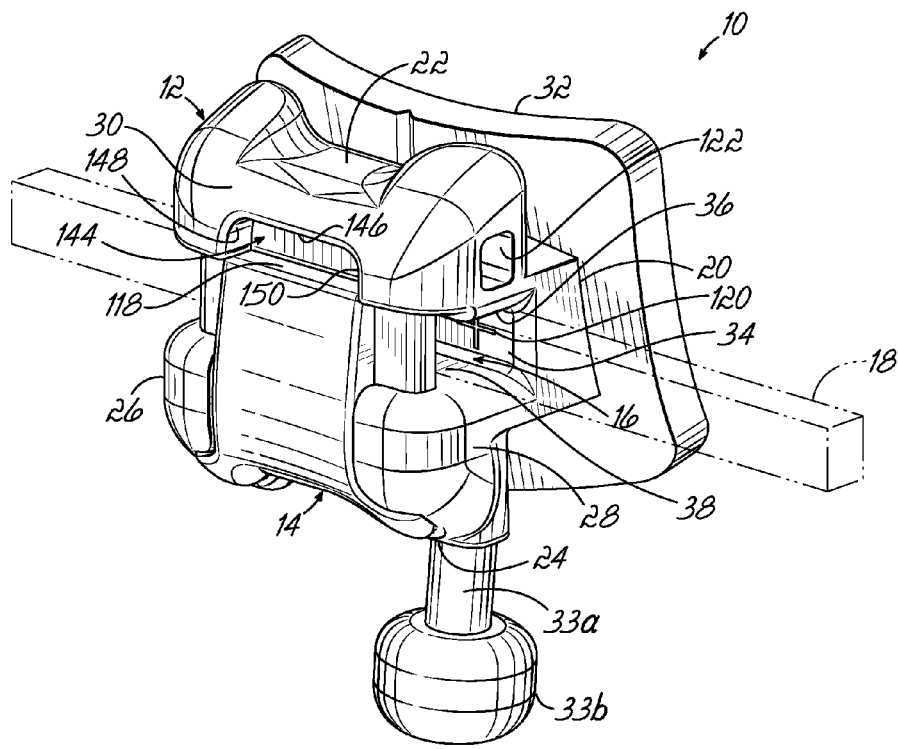
FIG. 2 is a perspective view of the self-ligating orthodontic bracket shown in FIG. 1 with the ligating slide shown in the closed position.

Referring now to the drawings, and to FIGS. 1 and 2 in particular, an orthodontic bracket 10 includes a bracket body 12 and a movable closure member coupled to the bracket body 12. In one embodiment, the movable closure member may include a ligating slide 14 slidably coupled with the bracket body 12. The bracket body 12 includes an archwire slot 16 formed therein adapted to receive an archwire 18 (shown in phantom) for applying corrective forces to the teeth. The ligating slide 14 is movable between an opened position (FIG. 1) in which the archwire 18 is insertable into the archwire slot 16 and a closed position (FIG. 2) in which the archwire 18 is retained within the archwire slot 16. The bracket body 12 and ligating slide 14 collectively form an orthodontic bracket 10 for use in corrective orthodontic treatments. Moreover, while the movable closure member is described herein as a ligating slide, the invention is not so limited as the movable closure member may include other movable structures (e.g., latch, spring clip, door, etc.) that are capable of moving between an opened and closed position.

The orthodontic bracket 10, unless otherwise indicated, is described herein using a reference frame attached to a labial surface of a tooth on the lower jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

Figure 12:
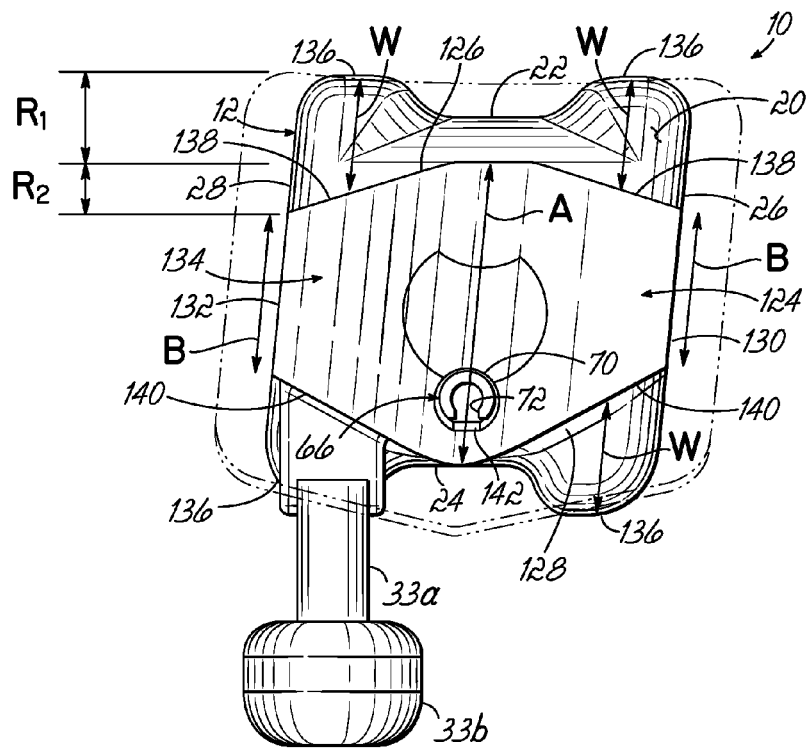
FIG. 12 is a rear elevation view of the self-ligating orthodontic bracket shown in FIG. 1.

When mounted to the labial surface of a tooth carried on the patient's lower jaw, the bracket body 12 has a lingual side 20, an occlusal side 22, a gingival side 24, a mesial side, 26, a distal side 28 and a labial side 30. The lingual side 20 of the bracket body 12 is configured to be secured to the tooth in any conventional manner, such as for example, by an appropriate orthodontic cement or adhesive or by a band around an adjacent tooth. The lingual side 20 may further be provided with a pad 32 defining a bonding base that is secured to the surface of the tooth (FIG. 12). The pad 32 may be coupled to the bracket body 12 as a separate piece or element, or alternatively, the pad 32 may be integrally formed with the bracket body 12. A coupling element in the form of, for example, an orthodontic hook having a shaft 33a and bulbous end 33b may extend from the bracket body 12 and facilitate coupling of the bracket body 12 with other orthodontic elements such as bands or other hooks on adjacent teeth. The bracket body 12 includes a base surface 34 and a pair of opposed slot surfaces 36, 38 projecting labially from the base surface 34 that collectively define the archwire slot 16 extending in a mesial-distal direction from mesial side 26 to distal side 28. The slot surfaces 36, 38 and base surface 34 are substantially encapsulated or embedded within the material of the bracket body 12. The archwire slot 16 of the bracket body 12 may be designed to receive the orthodontic archwire 18 in any suitable manner.

Figure 3:
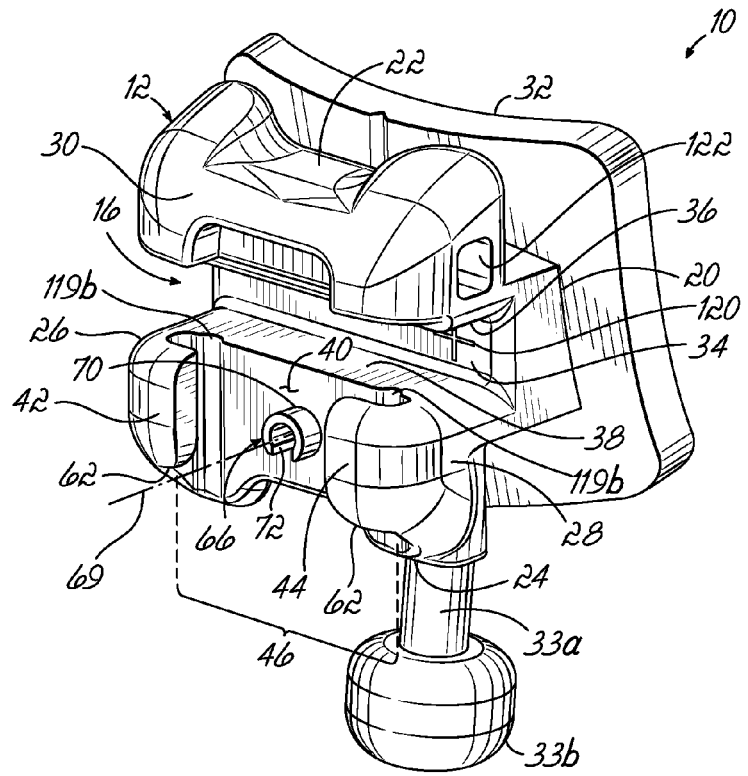
FIG. 3 is a perspective view of the self-ligating orthodontic bracket shown in FIG. 1 with the ligating slide removed from the bracket body.

As shown in FIG. 3, the bracket body 12 further includes a generally planar support surface 40 extending in a generally gingival-occlusal direction from slot surface 38. A pair of opposed guides 42, 44 are carried by support surface 40 and are positioned on respective mesial and distal sides 26, 28 of bracket body 12. The guides 42, 44 are generally L-shaped and each includes a first leg projecting from support surface 40 generally in the labial direction. Guide 42 has a second leg projecting in the distal direction while guide 44 has a second leg projecting in the mesial direction so that collectively, guides 42, 44 partially overlie support surface 40 in a spaced relation. Planar support surface 40 and guides 42, 44 collectively define a slide engagement track 46 for supporting and guiding ligating slide 14 within bracket body 12.

Figures 4A, 4B:
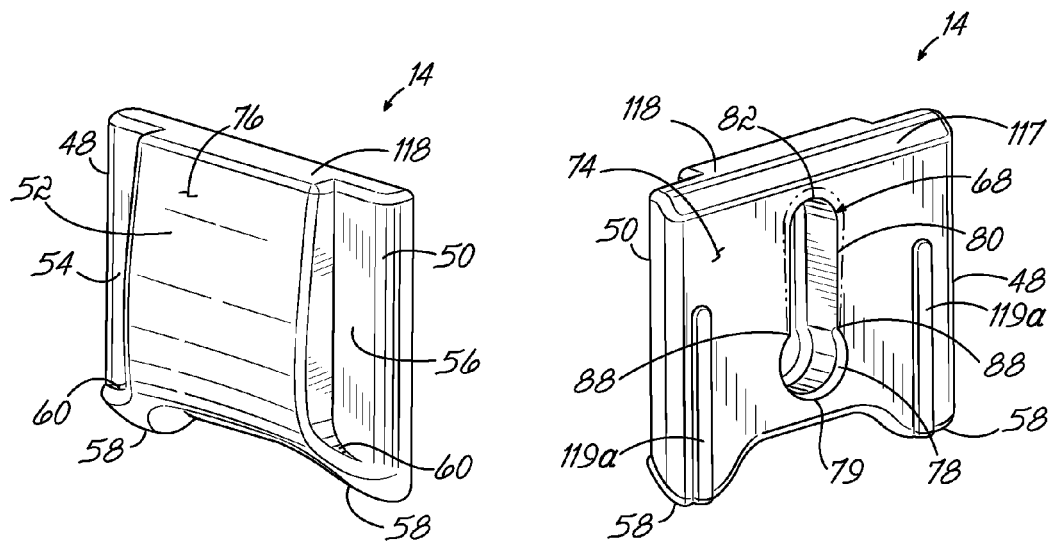
FIG. 4A is a front perspective view of the ligating slide shown in FIG. 1.
FIG. 4B is a rear perspective view of the ligating slide shown in FIG. 1.

As shown in FIGS. 4A and 4B, the ligating slide 14 is a generally planar structure comprising a mesial portion 48, a distal portion 50, and a central portion 52 intermediate the mesial and distal portions 48, 50. Guides 42, 44 overlie mesial and distal portions 48, 50, respectively, and central portion 52 projects in the labial direction such that the labial side of central portion 52 is substantially flush with the labial side of guides 42, 44 (FIG. 2). Such a configuration essentially defines gingival-occlusal directed tracks or grooves 54, 56 in the labial side of the ligating slide 14 along which guides 42, 44 move as the ligating slide 14 is moved between the opened and closed positions. In one embodiment, the gingival ends 58 of grooves 54, 56 may include stop portions 60 extending in the labial direction and closing off grooves 54, 56. The stop portions 60 are adapted to be adjacent or even abut a gingival end 62 of the guides 42, 44 (FIG. 3) when the ligating slide 14 is in the closed position (FIG. 2).

As shown in FIGS. 3 and 4B, the orthodontic bracket 10 includes a securing mechanism that secures the ligating slide 14 in at least the closed position. To this end, the securing mechanism includes a projecting portion in one of the bracket body 12 or ligating slide 14 and a receiving portion in the other of the bracket body 12 or ligating slide 14 that cooperate to keep the ligating slide 14 in at least the closed position, and may further prevent the ligating slide 14 from detaching from the bracket body 12. In one exemplary embodiment, the securing mechanism includes a generally elongated cylindrical, tubular spring pin 66 (FIG. 3) coupled to the bracket body 12 and a retaining slot 68 (FIG. 4B) formed in the ligating slide 14. Although this embodiment is described with the spring pin 66 associated with the bracket body 12 and the retaining slot 68 associated with the ligating slide 14, those of ordinary skill in the art will recognize that the invention is not so limited. For example, although not shown, the spring pin 66 may be coupled to the ligating slide 14 and the retaining slot 68 may be formed in the bracket body 12.

As shown in FIG. 3, the spring pin 66 extends along a central axis 69 and includes a first portion (not shown) received within a bore 70 formed in support surface 40 and a second portion that projects therefrom in a direction generally perpendicular to archwire slot 16, such as, for example, in a generally labial direction (e.g., the spring pin 66 projects generally in a labial-lingual direction). The spring pin 66 includes a cutout or slit 72, the purpose of which is described below, formed in the sidewall thereof and extends along at least a portion of the length of the spring pin 66. For example, the slit 72 may extend for the full length of the spring pin 66. Alternatively, the slit 72 may extend for at least the length of the second portion of the spring pin 66 which projects from support surface 40. Other slit configurations may also be possible.

The spring pin 66 may be formed, for example, through a rolling process so as to define the slit 72, or alternatively, may be formed by cutting a tubular member to form slit 72. Additionally, the spring pin 66 may be formed from materials including stainless steel, titanium alloys, NiTi-type superelastic materials, or other suitable materials. During assembly, the spring pin 66 may be press fit or slip fit into bore 70, and/or may be secured thereto to prevent relative movement therebetween using various processes including staking, tack welding, laser welding, adhesives, or other suitable methods.

As shown in FIG. 4B, the retaining slot 68 may be formed in the lingual side 74 of the ligating slide 14 and extends generally in the gingival-occlusal direction due to the general gingival-occlusal movement of ligating slide 14. The retaining slot 68 may be formed so as to extend completely through the ligating slide 14 in the labial-lingual direction (not shown), or formed so as to extend only partially through the slide 14, and therefore not be visible from the labial side 76 of the slide 14 (i.e., a blind slot), as shown in FIGS. 4A and 4B. Such a blind slot configuration reduces the sites on the labial side 30 of the bracket 10 where food or other material from the oral cavity could collect, thereby improving overall hygiene. In one embodiment, the retaining slot 68 has a first enlarged portion 78 at the gingival end 79 of the slot 68 in communication with a straight segment portion 80 having a closed occlusal end 82. The enlarged portion 78 may be generally circular, as shown, or have other suitable shapes. The cross dimension of the enlarged portion 78 is larger than the cross dimension of the straight segment portion 80 to define a pair of opposed protrusions 88 at the transition therebetween.

When the ligating slide 14 is coupled to the bracket body 12, the spring pin 66 is received in retaining slot 68, which moves relative to the spring pin 66 as the ligating slide 14 is moved between the opened and closed positions. In one aspect of the invention, the spring pin/retaining slot securing mechanism provides for securing the ligating slide 14 in at least the closed position. To this end, the slit 72 in the spring pin 66 allows at least the slit portion to be generally radially flexed or elastically deformed relative to its central axis 69. As used herein, radially flexed includes not only uniform radial changes, but also includes non-uniform or partial radial changes, such as that which occurs during squeezing of a resilient C clip. In other words, at least a portion of spring pin 66 has a first effective diameter or radius of curvature (such as in an unbiased state) but is capable of being flexed, such as by squeezing the spring pin 66, so as to have a second effective diameter or radius of curvature smaller than the first effective diameter or radius of curvature. Thus, the spring pin 66 is capable of radially expanding and contracting depending on the force being imposed thereon. While the slit 72 in spring pin 66 allows for radial contraction/expansion, such movement may be achieved in other ways. For example, the spring pin may be a thin-walled tubular member without such a slit yet still be capable of radial contraction/expansion. Those of ordinary skill in the art may recognize additional configurations that provide such radial contraction and expansion of spring pin 66.

In operation, when the ligating slide 14 is in the closed position (FIG. 2), the spring pin 66 is disposed in the enlarged portion 78 of retaining slot 68 and is permitted to radially expand such that the spring pin 66 engages the wall of circular portion 78. Those of ordinary skill in the art will recognize that the spring pin 66 does not have to engage the wall of circular portion 78, but must at least have a cross dimension (e.g., diameter) when radially expanded that is larger than the cross dimension of the straight segment portion 80. When so disposed in the circular portion 78, the protrusions 88 provide a threshold level of resistance to any movement of the ligating slide 14 away from the closed position and toward the opened position. However, if a sufficiently large opening force is applied to the ligating slide 14 in, for example, the gingival direction, the interaction between the retaining slot 68 and spring pin 66 causes the pin 66 to radially contract (due to the squeezing imposed by the slot 68) so that the spring pin 66 moves past the protrusions 88 and into the straight segment portion 80 of the retaining slot 68.

Once positioned in the straight segment portion 80, the spring pin 66 bears against the walls thereof such that a threshold sliding force, which may be less than, and perhaps significantly less than the opening force, must be imposed to overcome the drag and move the ligating slide 14 relative to the bracket body 12 as spring pin 66 traverses straight segment portion 80. Thus, once opened, the ligating slide 14 does not just freely slide or drop to the fully opened position, but must be purposefully moved toward the opened position. If the ligating slide 14 is only partially opened, the slide 14 may be configured to maintain its position relative to the bracket body 12 (due to the friction forces) until the threshold sliding force is imposed to continue moving the slide 14 toward the opened position. Such a configuration reduces the likelihood of unintentionally closing the slide during, for example, an orthodontic treatment. When the ligating slide 14 is moved toward the closed position, the spring pin 66 recovers or snaps back to its radially expanded position as the spring pin 66 enters the enlarged portion 78 to once again secure the ligating slide 14 in the closed position.

The amount of force required to overcome the threshold sliding force as the spring pin 66 moves relative to the straight segment portion 80 may vary during movement between the opened and closed positions of ligating slide 14. In one embodiment, for example, the straight segment portion 80 may be slightly tapered so that the cross dimension of straight segment portion 80 increases in the direction of the occlusal end 82 of the retaining slot 68. Such a configuration is shown in phantom in FIG. 4B. Accordingly, the sliding force required for relative movement between the spring pin 66 and the retaining slot 68 of ligating slide 14 decreases as the ligating slide 14 is moved toward the opened position and increases as the ligating slide 14 is moved toward the closed position. In addition to, or instead of, the tapered feature described above, a variable sliding force may be achieved by varying the depth of the retaining slot 68 in the ligating slide 14 so as to interact with the terminating end of spring pin 66 (not shown). For example, the depth of retaining slot 68 may be smaller adjacent the gingival end 79 as compared to the depth of the retaining slot 68 adjacent the occlusal end 82. Due to the interaction between the terminating end of the spring pin 66 and the bottom or base surface of retaining slot 68, the sliding force required for relative movement between the spring pin 66 and the retaining slot 68 decreases as the ligating slide 14 is moved toward the opened position and increases as the ligating slide 14 is moved toward the closed position. The above-described methods for varying the sliding force are exemplary and those of ordinary skill in the art may recognize other ways to vary the sliding force of the ligating slide 14 as the slide is moved between the opened and closed positions.

Figure 5:
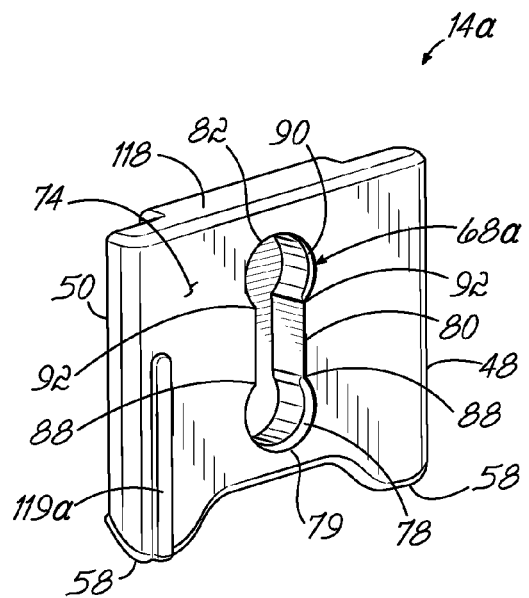
FIG. 5 is a rear perspective view of a ligating slide in accordance with another embodiment of the invention.

The retaining slot 68 shown in FIG. 4B, and as described above, includes enlarged portion 78 at the gingival end 79 of retaining slot 68 that operates to secure the ligating slide 14 in the closed position. In that embodiment, the occlusal end 82 of the retaining slot 68 does not include such an enlarged portion, but instead terminates in a closed end to straight segment portion 80. In an alternative embodiment, however, and as shown in FIG. 5, in which like reference numerals refer to like features in FIG. 4B, ligating slide 14a may include a retaining slot 68a that also includes an enlarged portion 90 (similar to enlarged portion 78) at the occlusal end 82 of retaining slot 68a. Similar to the above, the enlarged portion 90 defines protrusions 92 at the transition between straight segment portion 80 and enlarged portion 90. In this way, the ligating slide 14a may be secured in both the closed and opened positions so as to require a sufficiently high opening or closing force to initiate movement of the ligating slide 14a away from the closed or opened positions, respectively.

Similar to that described above, when the ligating slide 14a is in the closed position, the spring pin 66 is disposed in the enlarged portion 78 and a sufficiently large opening force must be applied to the ligating slide 14a in the gingival direction to contract spring pin 66 and allow the pin 66 to move past the protrusions 88 and into the straight segment portion 80. As the ligating slide 14a is moved further toward the opened position, the spring pin 66 snaps back to its radially expanded position as the spring pin 66 enters the enlarged portion 90 at the occlusal end 82 of the retaining slot 68a. When so disposed in enlarged circular portion 90, the protrusions 92 provide a threshold level of resistance to any movement of the ligating slide 14a away from the opened position and toward the closed position. Only after a sufficiently large closing force is applied to the ligating slide 14a in, for example, the occlusal direction, will the spring pin 66 radially contract so that spring pin 66 moves past the protrusions 92 and into the straight segment portion 80 of the retaining slot 68a. Such a configuration may further prevent or reduce the likelihood of inadvertently closing the ligating slide 14a during treatment, such as when changing the archwires.

In addition to sufficiently securing the ligating slide 14 in at least the closed position (and possibly in the opened and closed position), the spring pin/retaining slot securing mechanism may also prevent or reduce accidental or unintentional detachment of the ligating slide 14 from the bracket body 12 during use, such as when the ligating slide 14 is in the opened position. To this end, the length of the retaining slot 68 may limit the gingival-occlusal travel of ligating slide 14 relative to the bracket body 12. For example, the spring pin 66 may abut the occlusal end 82 of the retaining slot 68 when the ligating slide 14 is in the fully opened position. Because the occlusal end 82 closes the retaining slot 68, further movement of the ligating slide 14 in a gingival direction relative to bracket body 12 is prohibited, and ligating slide 14 cannot become separated or detached from bracket body 12.

Similarly, in the fully closed position of the ligating slide 14, the spring pin 66 is positioned in the enlarged portion 78 at the gingival end 79 of the retaining slot 68, which may prohibit further movement of the ligating slide 14 in the occlusal direction relative to the bracket body 12. The orthodontic bracket 10 may include other features that, in lieu of or in addition to, the spring pin/retaining slot securing mechanism prevents movement of the ligating slide 14 in the occlusal direction relative to the bracket body 12. Accordingly, the securing mechanism may operate for the dual function of securing the ligating slide 14 in the closed position (and possibly the opened position as well) and for retaining the ligating slide 14 with the bracket body 12. Such a dual-functioning securing mechanism may provide certain benefits not heretofore observed in brackets that utilize separate mechanisms for each of these functions.

Figure 6:
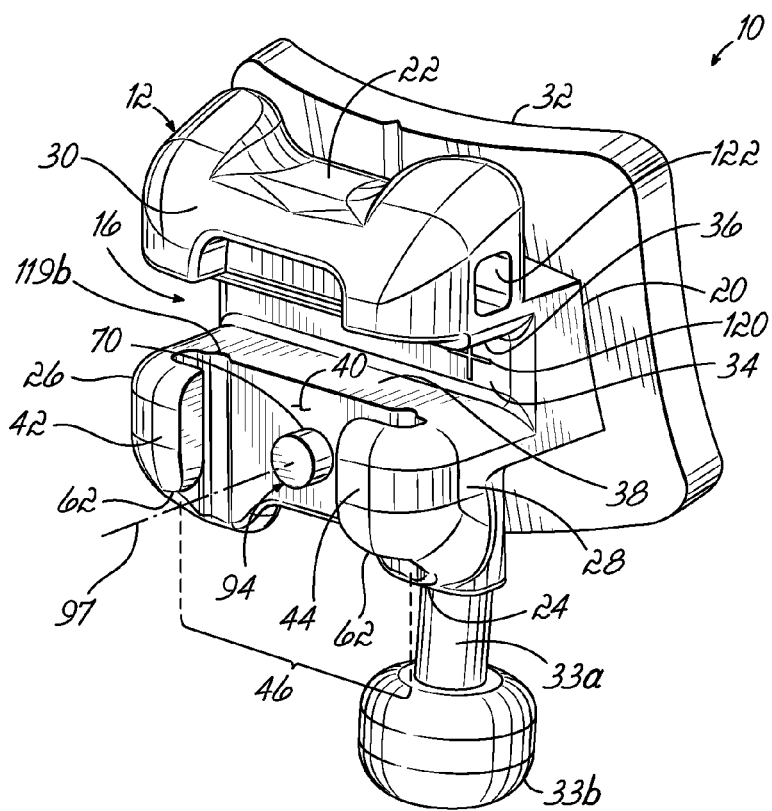
FIG. 6 is a perspective view of a self-ligating orthodontic bracket in accordance with another embodiment of the invention with the ligating slide removed from the bracket body.
Figure 7:
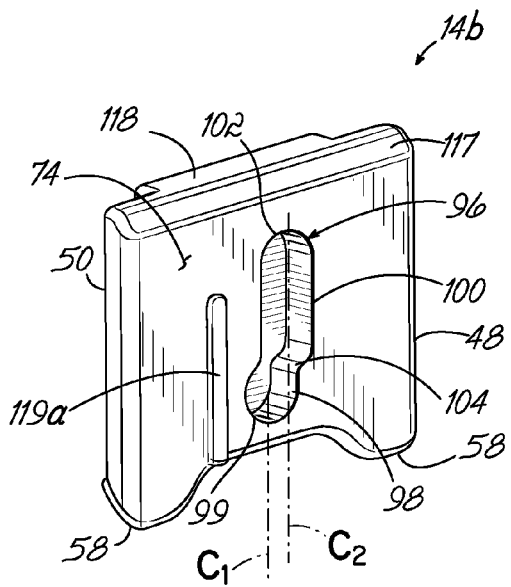
FIG. 7 is a rear perspective view of a ligating slide used with the orthodontic bracket shown in FIG. 6.

FIGS. 6 and 7, in which like reference numerals refer to like features in FIGS. 1-4, illustrate an alternative securing mechanism that secures the ligating slide 14b in at least the closed position. In this embodiment, the securing mechanism includes a solid generally elongated cylindrical retaining pin 94 coupled to the bracket body 12 and a retaining slot 96 formed in the ligating slide 14b. Although this embodiment is described with the retaining pin 94 associated with the bracket body 12 and the retaining slot 96 associated with the ligating slide 14b, those of ordinary skill in the art will recognize that the invention is not so limited. For example, although not shown, the retaining pin 94 may be coupled to the ligating slide 14b and the retaining slot 96 formed in the bracket body 12.

As shown in FIG. 6, the retaining pin 94 extends along a central axis 97 and includes a first portion (not shown) received within the bore 70 formed in support surface 40 and a second portion that projects therefrom in a generally labial direction. In this embodiment, the retaining pin 94 does not radially contract and expand, but instead is capable of lateral flexing or bending relative to its central axis 97 such that the retaining pin 94 is no longer straight, for example, but is slightly curved (not shown). The retaining pin 94 may be formed from materials including stainless steel, titanium alloys, NiTi-type superelastic materials, or other suitable materials. Additionally, during assembly, the retaining pin 94 may be press fit or slip fit into bore 70, and/or may be secured thereto to prevent any relative movement therebetween using various processes, including staking, tack welding, laser welding, adhesives, or other suitable methods.

As shown in FIG. 7, the retaining slot 96 is formed in the lingual side 74 of the ligating slide 14b and extends generally in the gingival-occlusal direction. As in the previous embodiments, the retaining slot 96 may extend completely through the ligating slide 14b or be formed as a blind slot and therefore not be visible from the labial side 76 of the ligating slide 14b (e.g., similar to FIG. 4A). In this embodiment, the retaining slot 96 includes an offset portion 98 at the gingival end 99 of the slot 96 in communication with a straight segment portion 100 having a closed occlusal end 102. A centerline $C_1$ of the offset portion 98 is displaced in the mesial-distal direction (distal displacement shown in FIG. 7) relative to a centerline $C_2$ of the straight segment portion 100 to form a protrusion 104 at the transition therebetween.

When the ligating slide 14b is coupled to the bracket body 12, the retaining pin 94 is received in retaining slot 96, which moves relative to the retaining pin 94 as the ligating slide 14b is moved between the opened and closed positions. The retaining pin/retaining slot securing mechanism provides for securing the ligating slide 14b in at least the closed position. To this end, and as noted above, the retaining pin 94 is capable of laterally flexing along its central axis 97. In other words, the retaining pin 94 has a first position (which may be an unbiased position wherein the retaining pin 94 is essentially straight) and is capable of being flexed out of the first position away from its central axis 97 so as to be slightly curved.

In operation, when the ligating slide 14b is in the closed position, the retaining pin 94 is disposed in the offset portion 98 and in its first position (e.g., relatively straight and unflexed). When so disposed in the offset portion 98, the protrusion 104 and/or the retaining pin 94 provides a threshold level of resistance to any movement of the ligating slide 14b away from the closed position and toward the opened position. If a sufficiently large opening force is applied to the ligating slide 14b in the gingival direction, however, the interaction between the retaining slot 96 and retaining pin 94 causes the pin 94 to be flexed away from the first position and to the second position so that the retaining pin 94 moves past the protrusion 104 and into the straight segment portion 100 of the retaining slot 96.

Once positioned in the straight segment portion 100, the retaining pin 94 is biased to return to its unbiased (or less biased first position) and thus bears against the mesial side wall of the retaining slot 96 such that a threshold sliding force, which may be less than, and perhaps significantly less than the opening force, must be imposed to overcome the drag and move the ligating slide 14b relative to the bracket body 12 as retaining pin 94 traverses straight segment portion 100. Thus, once opened, the ligating slide 14b does not just freely slide or drop to the fully opened position, but must be purposefully moved to the opened position. If the ligating slide 14b is only partially opened, the slide 14b may be configured to maintain its position relative to the bracket body 12 (due to the friction forces) until the threshold sliding force is imposed to continue moving it toward the opened position. When the ligating slide 14b is moved toward the closed position, the retaining pin 94 recovers or snaps back to its first position as the retaining pin 94 enters the offset portion 98 to once again secure the ligating slide 14b in the closed position.

Although not shown in the drawings, but similar to that described above in reference to FIGS. 4B and 5, in an alternative embodiment the retaining slot 96 may also be configured so as to provide a variable sliding force as the ligating slide 14b moves between the opened and closed positions. Moreover, the ligating slide 14b may include an offset portion at both the gingival and occlusal ends 99, 102 of the slot 96. In this way, the ligating slide 14b may be sufficiently secured in both the opened and closed positions in a similar manner to that described above in reference to FIG. 5.

In addition to sufficiently securing the ligating slide 14b in at least the closed position (and possibly in the opened and closed positions), the retaining pin/retaining slot configuration may also prevent accidental or unintentional detachment of the ligating slide 14b from the bracket body 12 during use. To this end, the length of the retaining slot 96 may limit the gingival-occlusal travel of ligating slide 14b relative to bracket body 12. For example, the retaining pin 94 may abut the occlusal end 102 of the slot 96 when the ligating slide 14b is in the fully opened position. Because the occlusal end 102 of slot 96 is closed, further movement of the ligating slide 14b in the gingival direction relative to bracket body 12 is prohibited, and ligating slide 14b cannot become separated or detached from bracket body 12.

Similarly, in the fully closed position of the ligating slide 14b, the retaining pin 94 may be positioned in the offset portion 98 at the gingival end 99 of the retaining slot 96, and further movement of the ligating slide 14b in the occlusal direction relative to the bracket body 12 may be prohibited. The bracket 10 may include other features that, in lieu of or in addition to, the retaining pin/retaining slot securing mechanism prevents movement of the ligating slide 14b in the occlusal direction relative to the bracket body 12. Accordingly, the securing mechanism may operate for the dual function of securing the ligating slide 14b in the closed position (and possibly the opened position as well) and for retaining the ligating slide 14b with the bracket body 12.

Figure 8:
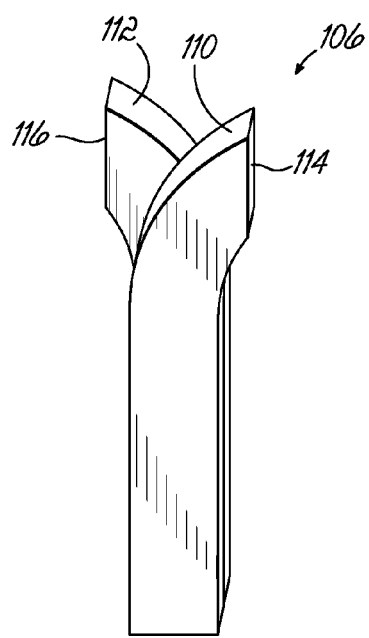
FIG. 8 is a perspective view of a spring bar in accordance with one embodiment of the invention.
Figure 9:
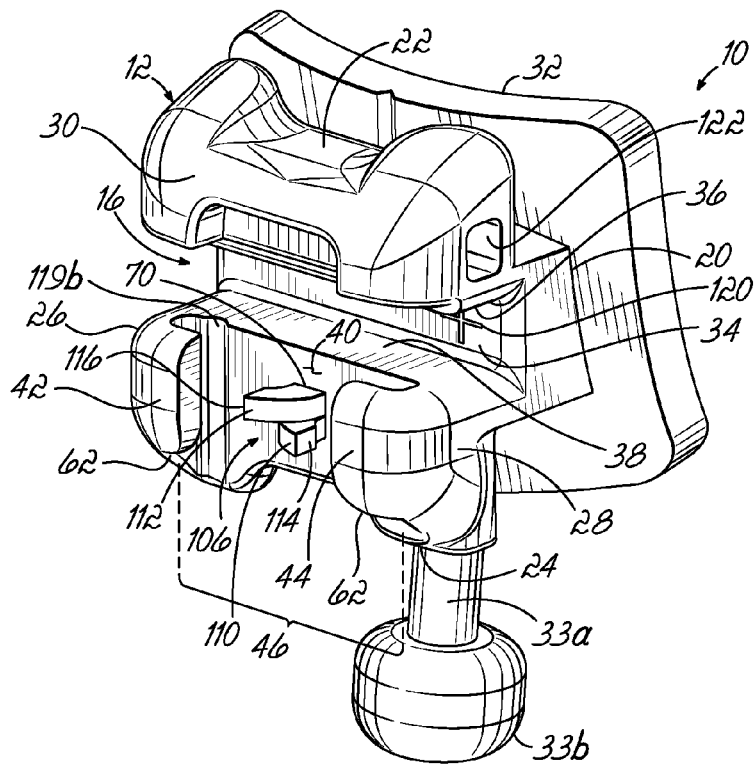
FIG. 9 is a perspective view of a self-ligating orthodontic bracket in accordance with another embodiment of the invention utilizing the spring bar of FIG. 8 and with the ligating slide removed from the bracket body.

FIGS. 8 and 9, in which like reference numerals refer to like features in FIGS. 1-4, illustrate another alternative securing mechanism that secures the ligating slide 14 in at least the closed position. In this embodiment, the securing mechanism includes a spring bar 106 coupled to the bracket body 12 and the retaining slot 68 formed in the ligating slide 14, as shown in FIG. 4B. Although this embodiment is described with the spring bar 106 associated with the bracket body 12 and the retaining slot 68 associated with the ligating slide 14, those of ordinary skill in the art will recognize that the invention is not so limited. For example, although not shown, the spring bar 106 may be coupled to the ligating slide 14 and the retaining slot 68 formed in the bracket body 12.

The spring bar 106 includes a first portion (not shown) received within the bore 70 formed in support surface 40 and a second portion that projects therefrom in a generally labial direction. In this embodiment, the second portion of spring bar 106 is configured as a pair of spring arms 110, 112 having opposed contacting end surfaces 114, 116 that are capable of being flexed toward each other, such as by squeezing the end surfaces 114, 116 toward each other. The spring bar 106 may be formed from materials including stainless steel, titanium alloys, NiTi-type superelastic materials, or other suitable materials. Additionally, during assembly, the spring bar 106 may be press fit or slip fit into bore 70, and/or may be secured thereto to prevent any relative movement therebetween using various processes including staking, tack welding, laser welding, adhesives, or other suitable methods. As shown in FIG. 9, the spring bar 106 may be oriented within bore 70 so that the end surfaces 114, 116 face in the mesial-distal direction so as to operate with retaining slot 68, as is described in more detail below.

When the ligating slide 14 is coupled to the bracket body 12, the spring bar 106 is received in retaining slot 68, which moves relative to the spring bar 106 as the ligating slide 14 is moved between the opened and closed positions. The spring bar/retaining slot securing mechanism provides for securing the ligating slide 14 in at least the closed position. To this end, and as noted above, the spring arms 110, 112 of spring bar 106 are capable of resiliently flexing so as to vary a dimension between end surfaces 114, 116 (e.g., expanding and contracting). In other words, the spring bar 106 defines a first dimension (such as in an unbiased state) and is capable of being flexed, such as by squeezing the end surfaces 114, 116 together, to define a second dimension less than the first dimension. Thus, the spring bar 106 is capable of expanding and contracting in a dimension (e.g., the mesial-distal dimension) depending on the bias being imposed thereon.

In operation, when the ligating slide 14 is in the closed position, the spring bar 106 is disposed in the enlarged portion 78 of retaining slot 68 and is permitted to expand such that the end surfaces 114, 116 of spring arms 110, 112 engage the wall of enlarged portion 78. Those of ordinary skill in the art will recognize that the end surfaces 114, 116 do not have to engage the wall of enlarged portion 78, but must at least have a dimension that is larger than the cross dimension of the straight segment portion 80. When so disposed in the enlarged portion 78, the protrusions 88 provide a threshold level of resistance to movement of the ligating slide 14 away from the closed position and toward the opened position. However, if a sufficiently large opening force is applied to the ligating slide 14 in, for example, the gingival direction, the interaction between the retaining slot 68 and spring bar 106 causes the dimension between the end surfaces 114, 116 to decrease or contract (due to the squeezing imposed by contact with the slot 68 at protrusions 88) so that the spring bar 106 moves past the protrusions 88 and into the straight segment portion 80 of the retaining slot 68.

Once positioned in the straight segment portion 80, the end surfaces 114, 116 bear against the walls thereof such that a threshold sliding force, which is less than, and perhaps significantly less than the opening force, must be imposed to overcome the drag and move the ligating slide 14 relative to the bracket body 12 as spring bar 106 traverses straight segment portion 80. Thus, once opened, the ligating slide 14 does not just freely slide or drop to the fully opened position, but must be purposefully moved toward the opened position. If the ligating slide 14 is only partially opened, the slide 14 may be configured to maintain its position relative to the bracket body 12 (due to the friction forces) until the threshold sliding force is imposed to continue moving it toward the opened position. When the ligating slide 14 is moved toward the closed position, the end surfaces 114, 116 of spring bar 106 recover or snap back to their expanded dimension as the spring bar 106 enters the enlarged portion 78 to once again secure the ligating slide 14 in the closed position.

In alternative embodiments, the retaining slot 68 may be configured so as to provide a variable sliding force as the ligating slide 14 moves between the opened and closed positions. Moreover, the ligating slide 14 may provide an enlarged portion at both the gingival and occlusal ends thereof. In this way, the ligating slide 14 may be secured in both the opened and closed positions in a similar manner to that described above.

In addition to sufficiently securing the ligating slide 14 in at least the closed position (and possibly in the opened and closed positions), the spring bar/retaining slot securing mechanism may also prevent accidental or unintentional detachment of the ligating slide 14 from the bracket body 12 during use. To this end, the length of retaining slot 68 may limit the gingival-occlusal travel of the ligating slide 14 relative to the bracket body 12. For example, the spring bar 106 may abut the occlusal end 82 of the slot 68 when the ligating slide 14 is in the fully opened position. Because the slot 68 is closed at the occlusal end 82, further movement of the ligating slide 14 in a gingival direction relative to bracket body 12 is prohibited, and ligating slide 14 cannot become separated or detached from bracket body 12.

Similarly, in the fully closed position of the ligating slide 14, the spring bar 106 may be positioned in the circular portion 78 at the gingival end 79 of the retaining slot 68, and further movement of the ligating slide 14 in the occlusal direction relative to the bracket body 12 may be prohibited. The bracket 10 may include other features that, in lieu of or in addition to, the spring bar/retaining slot securing mechanism prevents movement of the ligating slide 14 in the occlusal direction relative to the bracket body 12. Accordingly, the securing mechanism may operate for the dual function of securing the ligating slide 14 in the closed position (and possibly the opened position as well) and for retaining the ligating slide 14 with the bracket body 12.

Because self-ligating brackets allow the movable member (e.g., slide, latch, spring clip, etc.) to move independently of the bracket body to achieve proper operation of the bracket, many conventional self-ligating brackets provide one mechanism to secure or lock the movable member in the closed position and thereby retain the archwire in the archwire slot, and further provide a second mechanism, typically separate from and different than the first mechanism, to prevent the movable member from disengaging from the bracket body. While utilizing separate mechanisms to perform these aspects results in orthodontic brackets that operate for their intended purpose, it is desirable to have a single, compact mechanism that performs both a locking function (i.e., maintains the movable member in at least the closed position) and prevents the movable member from disengaging from the bracket body. Such a design may provide certain benefits not heretofore found using current self-ligating brackets. For example, one benefit from such a compact, dual-function design may be that the overall size of the orthodontic bracket is reduced. This in turn improves the appearance of the orthodontia by reducing the "metal mouth" appearance in a patient. Additionally, the number of parts and/or assembly steps may be reduced with such a design, which may reduce the overall manufacturing costs of the bracket. As described above, certain embodiments encompassed herein include a dual-function mechanism that may provide the benefits described above.

In addition to the various securing mechanisms described above, orthodontic bracket 10 may include several other features that provide benefits to the design of the bracket and/or to the implementation of the bracket during orthodontic treatment. By way of example, during orthodontic treatment, such as during initial installation or change-out of the archwire, it is not uncommon for the archwire to slightly protrude from the archwire slot of the brackets. Thus, in order to close the ligating slide on the brackets, the orthodontist has to push the archwire into the archwire slot, such as with a separate tool using one hand, and then close the movable member using the other hand. Such a process may become burdensome or cumbersome, especially when repeated for all the brackets in the oral cavity.

To address such a scenario, and as shown in FIG. 4B, in one embodiment, the ligating slide 14 may include a pushing element for guiding the archwire into the archwire slot. In this regard, ligating slide 14 may include a chamfer 117 formed on lingual side 74 of the ligating slide 14 and adjacent the occlusal edge 118 (e.g., leading edge). The chamfer 117 is configured to guide or push the archwire 18 into the archwire slot 16 as the ligating slide 14 is moved toward the closed position. In this way, for example, the process of closing the ligating slide 14 also positions (e.g., pushes) the archwire 18 within the archwire slot 16. Thus, a single operation (e.g., closing the ligating slide) accomplishes both tasks and simplifies the procedure for the orthodontist.

Figure 10:
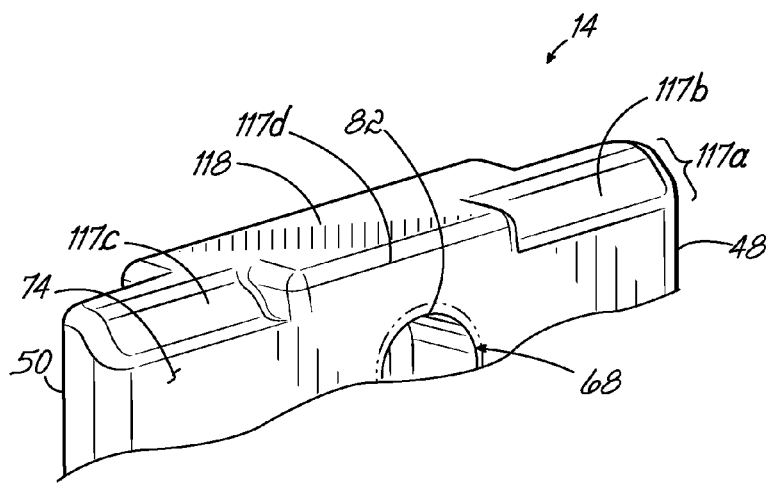
FIG. 10 is a partial rear perspective view of a ligating slide in accordance with one embodiment of the invention.

The chamfer 117 may be uniform and extend across the full extent of the occlusal edge 118 of the ligating slide 14, such as shown in FIG. 4B. However, in alternative embodiments, the chamfer may be non-uniformly formed along at least a portion of the occlusal edge 118. By way of example, as shown in FIG. 10, a chamfer 117a may include mesial and distal portions 117b, 117c, respectively, having a first chamfer configuration, and a central portion 117d having a second chamfer configuration, which may be different than the first chamfer configuration. Those of ordinary skill in the art will recognize that the chamfer configurations (which include very small chamfers or even no chamfer at all) on the mesial, distal, and central portions 117b-117d may each be different from the other depending on the specific application. Furthermore, although pushing of the archwire 18 into the archwire slot 16 may be achieved via a chamfer, as shown in the figures, other pushing elements are possible. For example, the occlusal edge 118 of the ligating slide 14 may include a rounded or radiused portion (not shown) to guide the archwire 18 into the archwire slot 16 as the ligating slide 14 is moved to the closed position.

Figure 15:
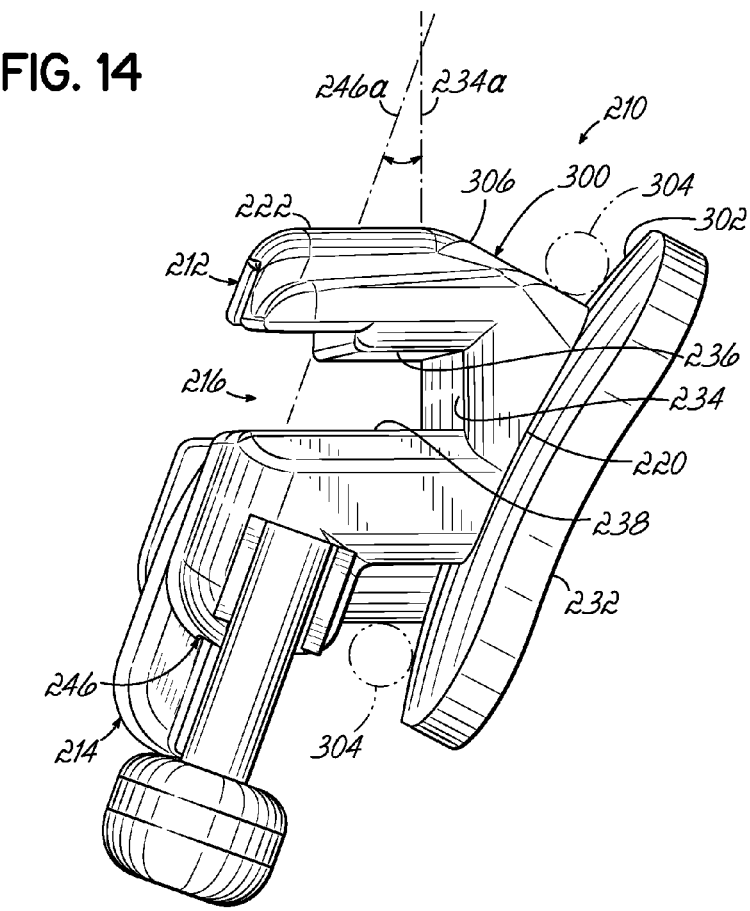
FIG. 15 is a side elevation view of the self-ligating orthodontic bracket shown in FIG. 14.

Another feature which may improve the manufacturing aspects of orthodontic bracket 10 includes a matching feature between the ligating slide 14 and the bracket body 12. As best illustrated in FIG. 3, the ligating slide 14 engages the bracket body 12 with a particular angle. As shown in FIG. 15 (in reference to a molar bracket), this angle may be quantified using the base surface 34 of the archwire slot 16 and the support surface 40 that defines at least in part the slide engagement track 46. Depending on where the orthodontic bracket 10 is located in the oral cavity, this angle may vary. By way of example, in one embodiment, this angle may be anywhere from approximately two degrees to approximately ten degrees for anterior teeth orthodontic brackets. As the bracket body 12 and ligating slide 14 are typically made in separate manufacturing processes, it is desirable to ensure that a bracket body 12 having a particular angled design matches with a ligating slide 14 having the same angled design (e.g., a two degree bracket is matched with a two degree ligating slide).

To this end, and in one embodiment, the lingual surface 74 of the ligating slide 14 may include one or more ribs 119a extending, for example, in a occlusal-gingival direction (FIGS. 4B and 5). Additionally, the support surface 40 of the bracket body 12 may include a corresponding number of grooves 119b formed therein configured to receive the ribs 119a when the ligating slide 14 is engaged with the bracket body 12 (FIG. 3). The number of ribs 119a and location of the ribs on the ligating slide 14 (and thus the location of grooves 119b on the bracket body 12) may vary for the different angles. In this way, only a ligating slide having the same angled design as the bracket body can mate with the bracket body during assembly. Thus, for example, a two-degree ligating slide will be matched with a two-degree bracket body and the problems associated with mismatched ligating slides and bracket bodies may be avoided. Those of ordinary skill in the art may recognize other matching systems to ensure that the proper ligating slide corresponds to a particular bracket body.

Another aspect or feature which may enhance the functionality and use of orthodontic bracket 10 includes indicia for indicating the amount of torque provided by the bracket. In conventional orthodontic treatment, the amount of torque applied to the tooth by the archwire is controlled by the configuration of the bracket body 12. In particular, the torque may be controlled by manipulating the angle between the lingual side 20 of the bracket (or the pad 32) and the base surface 34 of the archwire slot 16. Brackets may be provided to orthodontists in various delineated categories. For example, brackets may be supplied to orthodontists having a: i) low torque; ii) standard torque; or iii) high torque. The amount of torque depends on the specific treatment and is thus made by the orthodontist on a case-by-case basis. In any event, current brackets provide no marking thereon to indicate which torque category the bracket belongs. Thus, such a determination is typically made by a visual inspection of the bracket, which may be difficult and may lead to the incorrect or undesired bracket being used for treatment.

To address such a situation, and as best shown in FIGS. 1 and 3, the orthodontic bracket 10 may include indicia 120 that indicates the torque category of the bracket 10. For example, in one embodiment, the indicia may include a plus sign (+) for a high torque bracket; a minus sign (−) for a low torque bracket; and no indicating mark for a standard torque bracket. While the plus and minus signs are discussed herein, the invention is not so limited as any set of symbols (or the lack of a symbol) may be used to indicate to the orthodontist the torque category of the bracket. For example, letters may be used that are indicative of the torque category. The use of letters for indicating torque (H for high torque; L for low torque) is disclosed in commonly owned U.S. application Ser. No. 11/685,540 filed on Mar. 13, 2007, the disclosure of which is incorporated by reference herein in its entirety. In this way, the orthodontist may easily determine the torque category and avoid the costs and aggravation of replacing brackets due to incorrect torque determinations.

A further feature which may enhance the functionality and use of orthodontic bracket 10 includes a horizontal slot formed in the bracket body 12. As shown in FIGS. 1-3, bracket body 12 may include a horizontal slot 122 generally aligned parallel to the archwire slot 16 and configured for receiving temporary attachment devices, such as, for example, a removable hook (not shown). Heretofore, slots (typically vertical slots) have been provided in brackets to couple conventional orthodontic devices, such as torquing springs, auxiliary archwires, and in general, more permanent type of devices, to the brackets. In one embodiment, the horizontal slot 122 extends from the mesial side 26 to the distal side 28 of the bracket body 12 to form one continuous horizontal slot. In an alternative embodiment, however, a first slot may be open to the mesial side 26 of the bracket body 12 and a second slot open to the distal side 28 of the bracket body 12 without communication therebetween.

The horizontal slot 122 may provide additional advantages in regard to temporary anchoring devices. A recent trend in orthodontic treatment is to establish a fixed reference point within the oral cavity and use the reference point to apply forces to the teeth so as to effect treatment thereof. In this regard, the fixed reference point may be established by a temporary anchoring device, which includes an anchor, such as a bone screw, that is removably coupled to the mandibular and/or maxillary jaw, depending on which dental arch is being treated. The anchor fixes the location of the temporary anchoring device within the oral cavity. The temporary anchoring device is then coupled to other orthodontic devices, such as brackets, to move the teeth into a desired position and/or orientation. The connection between the temporary anchoring device and an orthodontic bracket, for example, is sometimes difficult and may entail an ad hoc approach to achieve the connection. In an advantageous aspect, the horizontal slot 122 in the bracket body 12 provides a convenient manner in which to couple the orthodontic bracket 10 to a temporary anchoring device. The use of a horizontal slot 122 in the bracket 10 to achieve such a connection with a temporary anchoring device has heretofore not been recognized or appreciated in the art. Such a connection, however, overcomes many of the problems and ad hoc approaches associated with using such temporary anchoring devices.

As noted above, it may be desirable to reduce the size of the orthodontic bracket to improve the aesthetic aspects of orthodontia treatment. The improved securing mechanisms described above may allow the bracket to have a reduced size. For example, in some embodiments the size of the orthodontic bracket 10 in the gingival-occlusal direction may be about 0.124 inches, whereas conventional brackets are typically about 0.144 inches. Although reducing the size of the bracket is desirable, it is preferable that this reduction be achieved without negatively impacting other functional and desirable aspects of orthodontic brackets. By way of example, orthodontic brackets may include tie wings, which typically extend from the occlusal and/or gingival sides of the bracket body 12, that facilitate coupling of the bracket to other adjacent orthodontic devices using ligatures, elastic bands, or other connecting members known in the art. Reducing the size of the bracket may potentially reduce the height or extent of the tie wing so that the ability to secure a ligature or other connecting member to the tie wing becomes problematic.

Figure 11:
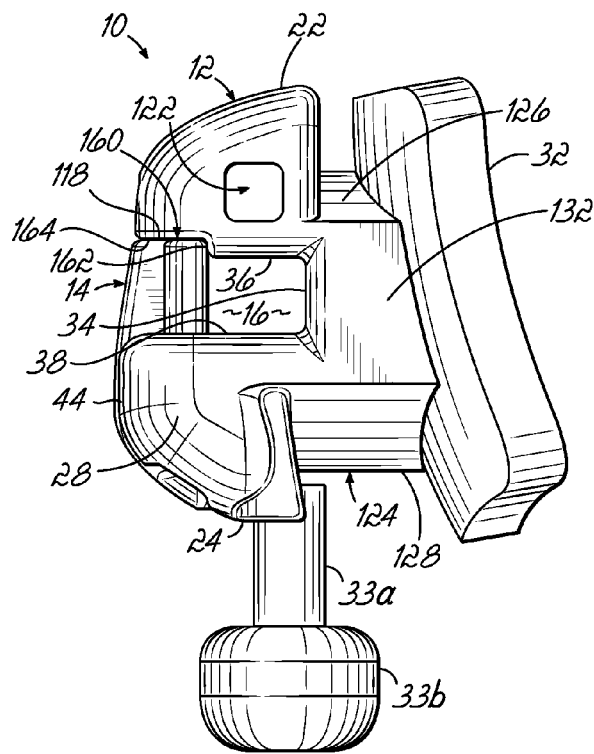
FIG. 11 is a side elevation view of the self-ligating orthodontic bracket shown in FIG. 1.

Accordingly, in still a further aspect of orthodontic bracket 10, the functional aspects of the tie wings may be retained while achieving a reduction in the size of the bracket, such as in the gingival-occlusal direction. To this end, and as shown in FIGS. 11 and 12, in which like reference numerals refer to like features in FIGS. 1-4, the lingual side 20 of the bracket body 12 includes a projecting portion 124 that couples to a tooth (not shown) or pad 32, as shown in FIG. 11. The projecting portion 124 includes an occlusal surface 126, a gingival surface 128, a mesial surface 130, a distal surface 132, and a lingual surface 134 that couples to pad 32, for example. The projecting portion 124 is configured to allow effective use of tie wings 136, as shown in FIG. 12. In this regard, the gingival-occlusal extent or height of the projecting portion 124 may be varied in a mesial-distal direction to facilitate use of the tie wings 136.

As shown in FIG. 12, the projecting portion 124 has a mesial-distal dimension substantially equal to the mesial-distal dimension of a more labial portion of the bracket body 12. For example, as shown in FIG. 12, the mesial side 26 of the bracket body 12, which includes mesial surface 130 of the projecting portion 124, is generally smooth and continuous. Similarly, the distal side 28 of the bracket body 12, which includes distal surface 132, is also generally smooth and continuous (FIG. 11). However, because the tie wings 136 are located along the occlusal and gingival sides 22, 24 of the bracket body 12 and generally extend therefrom, there is a reduction in the gingival-occlusal dimension of the projecting portion 124 relative to the more labial portion of the bracket body 12 having tie wings 136, as shown in FIG. 11. Such a reduction, indicated by $R_1$ in FIG. 12, is due to the nature of a tie wing based orthodontic bracket.

Moreover, typical tie wing brackets generally position the tie wings adjacent the mesial and distal sides of the bracket body. Thus, in accordance with one embodiment, the gingival-occlusal dimension of the projecting portion 124 adjacent the mesial and distal surfaces 130, 132 may be further reduced so as to effectively increase the working height of the tie wings 136. This further reduction is indicated by $R_2$ in FIG. 12. As shown in this figure, projecting portion 124 has a gingival-occlusal dimension A intermediate the mesial and distal surfaces 130, 132 and a gingival-occlusal dimension B adjacent the mesial and distal surfaces 130, 132 that is less than the dimension A. The dimension A may be determined by design considerations such as strength, rigidity, structural integrity, or other factors. As further illustrated in FIG. 12, however, the reduction to dimension B adjacent the mesial and distal surfaces 130, 132 relative to the intermediate dimension A provides an effective increase in the working height W of the tie wings 136 thereby providing enhanced functionality thereof.

In one embodiment, for example, such an increase in the working height W of the tie wings 136 (alternatively the further reduction of the gingival-occlusal height of the projecting portion 124) may be achieved by forming chamfers in the occlusal and gingival surfaces 126, 128. In particular, and as shown in FIG. 12, the occlusal surface 126 of projecting portion 124 may slope in a gingival direction from a mesial-distal intermediate location to the mesial-distal surfaces 130, 132 thereof to form chamfers 138. In a similar manner, the gingival surface 128 of projecting portion 124 may slope in an occlusal direction from a mesial-distal intermediate location to the mesial-distal surfaces 130, 132 thereof to form chamfers 140. Those of ordinary skill in the art will recognize that the length, degree and other characteristics of chamfers 138, 140 may vary (together or relative to each other) depending on the specific application. Those of ordinary skill in the art will further recognize other configurations that reduce the gingival-occlusal dimension relative to an intermediate dimension so as to increase the working height W of the tie wings 136.

In yet another aspect of orthodontic bracket 10, in various embodiments utilizing the spring pin 66 as part of the securing mechanism, it may be desirable to prevent relative rotation between the spring pin 66 and the bore 70 in bracket body 12. One reason for this may be, for example, to prevent the slit 72 in spring pin 66 from becoming aligned with the protrusions 88 in retaining slot 68 which may diminish the ability of the spring pin 66 to expand and contract in the desired manner. While this may be achieved using the various processes provided above (e.g., staking, welding, adhesives, etc.), in another embodiment, and as best illustrated in FIG. 12, rotation of the spring pin 66 relative to bore 70 may be prevented by forming a flat 142 in the generally circular bore 70. The spring pin 66 is inserted into the bore 70 such that the slit 72 therein is aligned with the flat 142, as shown in FIG. 12. Consequently, attempts to rotate the spring pin 66 relative to the bore 70 results in the edges that define slit 72 contacting the flat 142, thus preventing any relative rotation therebetween.

Figure 13:
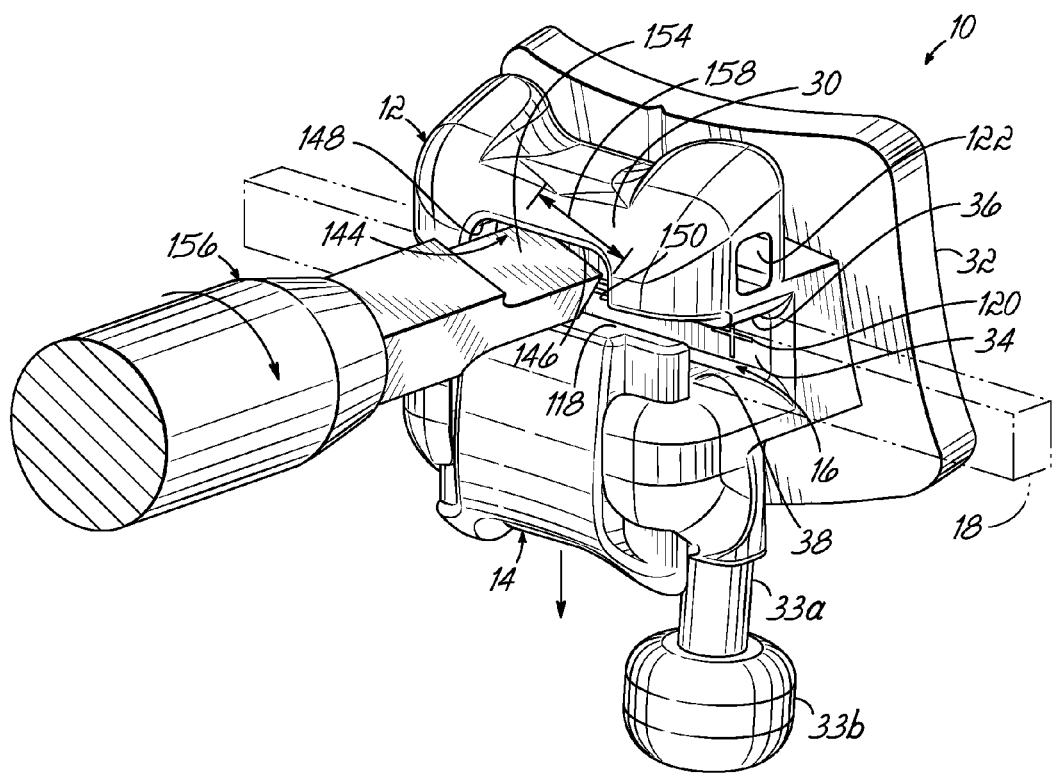
FIG. 13 is a perspective view of the self-ligating orthodontic bracket shown in FIG. 1 engaged with a tool for opening the ligating slide.

A further feature which may enhance the functionality and use of orthodontic bracket 10 includes a tool receptacle that cooperates with a tool for moving the ligating slide 14 away from the closed position and toward the opened position in an improved manner. With reference to FIGS. 2 and 13, the labial side 30 of bracket body 12 may include a tool receptacle 144 defining an occlusal wall 146, a mesial wall 148, and a distal wall 150. The receptacle 144, however, is open along a gingival end thereof so as to be accessible to at least a portion of ligating slide 14. For example, the tool receptacle 144 may be open to the occlusal edge 118 of ligating slide 14. As shown in FIG. 13, the tool receptacle 144 may be configured to receive the tip 154 of a tool 156 that facilitates opening the ligating slide 14 in a manner described below. While a wide range of screwdriver-type devices may be used to open ligating slide 14, it is contemplated that a tool, such as that disclosed in commonly owned U.S. application Ser. No. 12/147,854, filed on Jun. 27, 2008, and titled "Self-Ligating Orthodontic Bracket, Tools for use with a Self-Ligating Orthodontic Bracket, and Methods for Using such Tools," the disclosure of which is incorporated by reference herein in its entirety, may be used to open the ligating slide 14.

In operation, the tip 154 of the tool 156 is inserted into the tool receptacle 144 and rotated in either the clockwise or counter clockwise direction (clockwise shown in FIG. 13). As a result, a portion of the tip 154 bears against the occlusal wall 146 of the receptacle 144 and another portion of the tip 154 bears against the occlusal edge 118 of the ligating slide 14. The torque applied to the tool 156, such as by a user, is sufficient to overcome the opening force imposed by the securing mechanisms, as described above, such that the ligating slide 14 moves in the gingival direction relative to the bracket body 12 toward the opened position. The tool 156 may continue moving the ligating slide 14 until the tool 156 has been rotated about ninety degrees from its original position within receptacle 144.

In one aspect in accordance with this embodiment, the maximum length 158 of the tip 154 of tool 156 should not exceed the length of travel of the ligating slide 14 relative to the bracket body 12. Thus, in various embodiments described above, the length 158 of tip 154 should not exceed the length of the retaining slot 68 in the ligating slide 14, for example. In this way, when the tool 156 has been rotated to its full ninety-degree position, for example, the spring pin 66 has not yet reached the occlusal end 82 of the retaining slot 68. Such a configuration avoids shearing, notching, or otherwise damaging the spring pin 66 by torquing tool 156 and potentially rendering the orthodontic bracket 10 inoperable.

While the embodiment described above illustrates the tool receptacle 144 as being formed substantially within the bracket body 12, the invention is not so limited. For example, the tool receptacle may be formed substantially within the ligating slide such that, for example, the occlusal end of the tool receptacle is open and a tool inserted therein may contact a gingival edge of the bracket body 12 (e.g., see FIG. 27). In another alternative embodiment, part of the tool receptacle may be formed in the bracket body and part of the tool receptacle may be formed in the ligating slide (not shown).

The tool receptacle 144 as described above and more fully described in commonly owned U.S. application Ser. No. 12/147,854, filed on Jun. 27, 2008, and titled "Self-Ligating Orthodontic Bracket, Tools for use with a Self-Ligating Orthodontic Bracket, and Methods for Using such Tools," may provide some advantages. For example, the orthodontic bracket 10 including a tool receptacle 144 as described above, and methods of using tool 156 for opening the ligating slide 14 may permit a decrease in the force transmitted to the tooth of the patient. In particular, because the tool receptacle 144 results in contact of the opening tool 156 with both the ligating slide 14 and the bracket body 12, forces that would otherwise be transmitted to the tooth of the patient may be transmitted to the bracket body 12. In essence, the forces applied to the orthodontic bracket 10 as a whole during the opening of the ligating slide 14 effectively cancel each other out so that a negligible net force is transmitted to the tooth of the patient. Such a balancing out of the forces applied during opening of the ligating slide 14 prevents or reduces the discomfort associated with the transmission of a force to the tooth of the patient.

In another aspect of orthodontic bracket 10, and as best shown in FIG. 11, the ligating slide 14 may be configured to "overshoot" the archwire slot 16, and in particular, overshoot slot surface 36. To this end, a cutout 160 may be formed in the labial side 30 of the bracket body 12 adjacent slot surface 36 that defines a ledge 162 which extends above slot surface 36 and which is configured to engage the lingual side 74 of ligating slide 14 when the ligating slide 14 is in the closed position. Providing such an overshoot eases the acceptable tolerances in the coupling of the ligating slide 14 and bracket body 12 so as to cover the archwire slot 16 when in the closed position (e.g., precise tolerances are not required), but allows for the possibility that the occlusal edge 118 of the slide 14 may not abut an occlusal wall 164 of the cutout 160.

The use of conventional self-ligating brackets on molar teeth have presented some challenges to orthodontists and manufacturers of orthodontic brackets. For example, the size of conventional self-ligating brackets may create occlusion problems between the bracket and the teeth on the opposing jaw. Another problem is that prior self-ligating brackets have ligating slides that engage the bracket body from below and travel along guides in the bracket body that are substantially parallel to the gingival-occlusal plane. Moreover, when in an opened position, the bottom edge of the ligating slide extends below the bracket body. Thus, if conventional self-ligating brackets were attached to the molar teeth on the lower jaw, for example, the bottom edge of the ligating slide might contact gum tissue (gingiva) causing patient discomfort. Furthermore, in such situations, because gingival interference with the ligating slide might be significant, the slide could not be fully opened to accept an archwire, thus defeating an advantage of self-ligating brackets.

A design for a self-ligating orthodontic bracket for molar teeth that addresses many of these disadvantages has been proposed in commonly assigned U.S. Pat. No. 7,267,545, the disclosure of which is incorporated by reference herein in its entirety. As more fully disclosed therein, to avoid contact between the ligating slide and the gingiva as the slide is moved between the opened and closed position, the ligating slide may be angled with respect to the bracket body. In this regard, as the ligating slide is moved in the gingival direction toward the opened position, the gingival edge of the ligating slide moves in the labial direction and away from the gingiva. Furthermore, to avoid contact between the occlusal side of the bracket body and the teeth on the opposing jaw, the occlusal side of the bracket may be contoured or profiled such that as the teeth are brought together, there is no interference between the bracket and the teeth on the opposing jaw.

However, during various orthodontic treatments, it may be desirable to couple the molar bracket to adjacent orthodontic devices using ligature wire, elastic bands, or other connecting members known in the art. For example, it may be desirable to couple the bracket on the first molar to the bracket on the second molar so as to create a relatively strong anchor for effecting orthodontic treatment. Due to the space limitations in the rear of the oral cavity, as well as the desire to avoid contact with the gingiva and opposing teeth, tie wings are typically omitted from molar brackets. Accordingly, the bracket as a whole may be used to secure the ligature, band, etc. thereto.

Securing ligatures or elastic bands to self-ligating molar brackets, however, have presented some drawbacks. In particular, such brackets may lack suitable attachment points for receiving the ligature or elastic band and for maintaining the ligature or band at a relatively fixed location relative to the bracket. This may particularly be the case, for example, along the occlusal side of the molar bracket. As noted above, the occlusal side of molar self-ligating brackets may be contoured, such as by being directed downwardly in a gingival direction (when carried on the lower jaw, for example), to avoid contact with the teeth on the opposing jaw. While effective to avoid contact with the opposing teeth, such contouring may allow a ligature or band secured around the bracket to slide along the occlusal side of the bracket. Such movement of the ligature or band may be undesirable and may diminish the effectiveness of the treatment.

Figure 14:
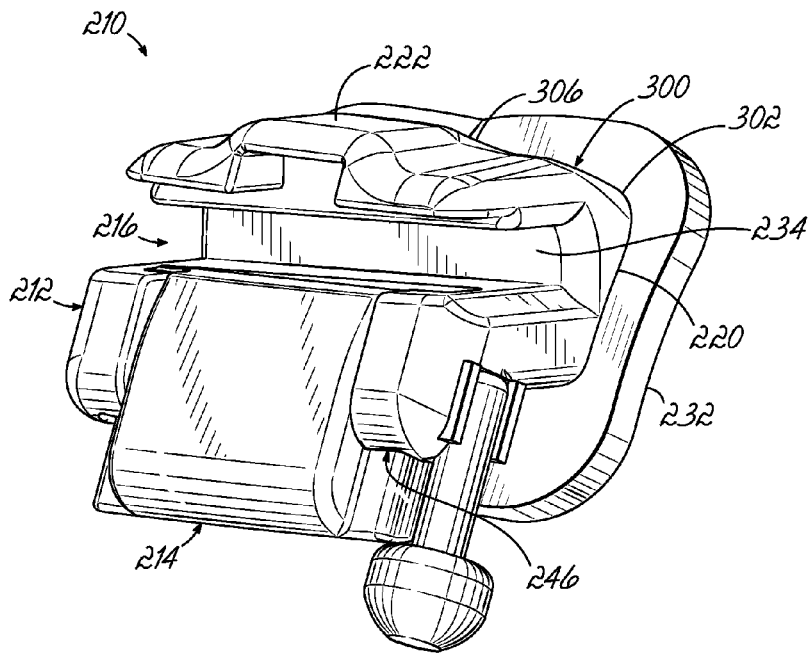
FIG. 14 is a perspective view of a self-ligating orthodontic bracket in accordance with another embodiment of the invention.

Improvements to molar self-ligating brackets, such as the brackets disclosed in U.S. Pat. No. 7,267,545, are thus desirable for addressing such a shortcoming. As shown in FIGS. 14 and 15, a self-ligating molar bracket 210 has features similar to that shown in FIGS. 1-4 and those features have similar reference numbers but are preceded by the number 2. In accordance with the disclosure of U.S. Pat. No. 7,267,545, and as clearly illustrated in these figures, the ligating slide 214 moves along a slide engagement track 246 that is angled relative to the base surface 234 of the archwire slot 216. In this regard, engagement track 246 extends generally along a translation plane 246*a* that is angled relative to a base plane 234*a* associated with the base surface 234. In addition, occlusal side 222 of the bracket body 212 may be generally contoured by directing at least a portion of the occlusal side 222 in a labial-gingival direction (i.e., slopes downwardly in reference frame of drawing).

To improve the functionality and use of molar self-ligating bracket 210 relative to the use of ligatures, elastic bands, etc., the occlusal side 222 of the bracket body 212 may include a cutout 300 adjacent the lingual side 220 thereof. The cutout 300 defines a groove 302 configured to receive a connecting member, such as a ligature or band 304, schematically shown in phantom in FIG. 15. The groove 302 is bounded in the labial-lingual direction so as to prevent or reduce the likelihood of movement of the ligature or band 304 relative to the bracket body 212 during use. For example, the groove 302 may be V-shaped, U-shaped, or have some other shape that facilitates the capture of a ligature or band therein. In one embodiment, as shown in FIG. 15, the groove 302 may be bounded in the labial direction by a sloped bounding surface 306 of the occlusal side 222, and may be bounded by the pad 232 in the lingual direction. The bounding surface 306 may be angled so as to generally face the tooth (i.e., has a surface normal that points toward the tooth) while the remainder of the occlusal side 222 generally faces away from the tooth (i.e., has a surface normal that points away from the tooth). Such a configuration maintains the ligature or band 304 in a relatively fixed location relative to the bracket body 212 and, in particular, prevents the ligature or band 304 from sliding in a labial direction along the occlusal side 222 of the bracket 210 and away from the tooth during use.

In addition to the improvement to the occlusal side 222, the orthodontic bracket 210 may incorporate other features as disclosed in the previous embodiments. By way of example, the bracket 210 may incorporate one of the securing mechanisms described above, the torque indicia, the horizontal slot, the tool receptacle, the chamfer or radiused feature at the occlusal end of the ligating slide, the matching system between ligating slide and bracket body, and/or other features described more fully above. Thus, aspects described for orthodontic bracket 10 may also provide benefits to molar brackets. Additionally, ligating slide 214 may include other features more fully disclosed in U.S. Pat. No. 7,267,545. By way of example, the lingual side 274 of ligating slide 214 may be angled adjacent the occlusal edge so that the archwire slot 216 more closely conforms to the cross-sectional shape of the archwire (now shown). In this regard, in one embodiment, ligating slide 214 cooperates with bracket body 212 to define a generally rectangular archwire slot 216 when the ligating slide 214 is in the closed position.

Manufacturers of orthodontic brackets continually seek improvements to bracket designs that provide greater comfort and greater reliability. For example, many conventional orthodontic brackets include labial surfaces that are irregular or discontinuous. In some situations, these irregularities may cause discomfort to the patient as, for example, soft oral tissue repeatedly engages the labial surface of the bracket. This discomfort or irritation may be particularly acute for rear portions of the oral cavity (e.g., brackets on the molar teeth) as oral tissue is generally tighter relative to more anterior portions of the oral cavity. Moreover, many conventional brackets include regular, generally planar exterior surfaces. During mastication, food or other material in the oral cavity impacts against these surfaces. These surfaces are arranged such that, instead of deflecting the material away from the bracket, a substantial portion of the mastication force is transferred to the orthodontic bracket. The increased forces transferred to the bracket increase the chances of breaking the bracket or otherwise preventing proper operation thereof.

Figure 16:
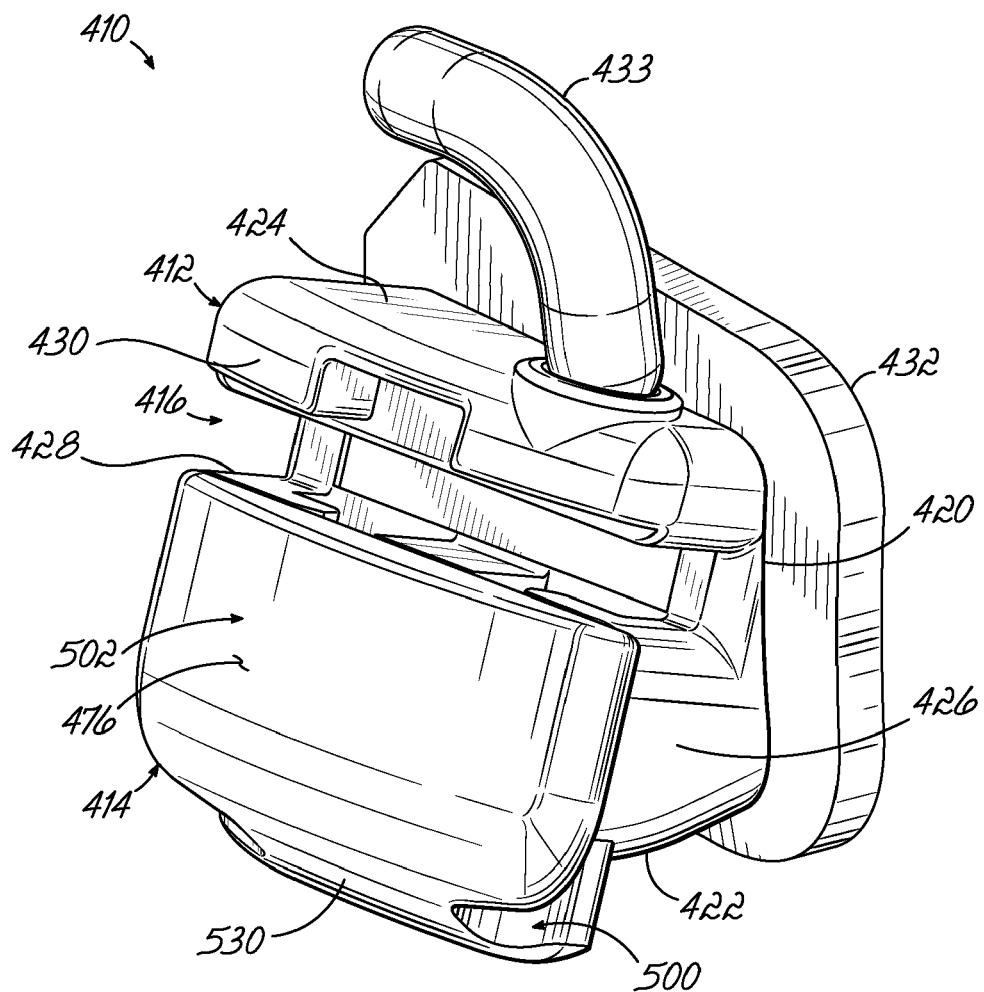
FIG. 16 is a perspective view of a self-ligating orthodontic bracket in accordance with another embodiment of the invention.

FIG. 16 illustrates an orthodontic bracket 410 designed to address these and other shortcomings. The bracket 410 has features similar to that shown in FIGS. 1-4 and those features have similar reference numerals but are preceded by the number 4. The bracket 410 as shown in the figures is configured and described for an upper molar tooth. However, as discussed above, those of ordinary skill in the art will appreciate that features of the bracket 410, as described below, may apply to brackets on other teeth, in different orientations, and/or in different areas of the oral cavity.

In one aspect in accordance with this embodiment, to increase patient comfort, the labial side 430 of the orthodontic bracket 410 is configured to be relatively smooth and continuous. By way of example, a smooth and continuous feature to bracket 410 may be accomplished using generally large radius of curvature surfaces and/or transitions between adjacent sides of the bracket 410. Such a configuration may be achieved primarily by modifying the design of the ligating slide 414. The design of the bracket body 412, however, may also be modified to achieve improved comfort. In one embodiment, the bracket body 412 generally includes a planar support surface 440 and a pair of opposed guides 442, 444 that collectively define a T-shaped slide engagement track 446 for ligating slide 414. Unlike the previous embodiments, however, the guides 442, 444, do not overlie the labial surface 476 of ligating slide 414 (e.g., contrast FIGS. 1 and 16, for example).

Figure 17:
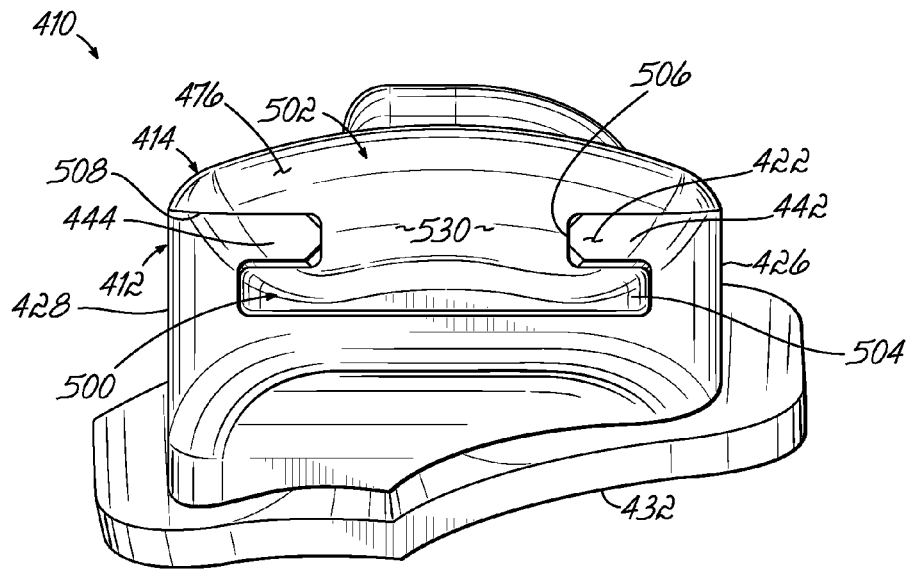
FIG. 17 is a bottom elevation view of the self-ligating orthodontic bracket shown in FIG. 16.
Figure 19:
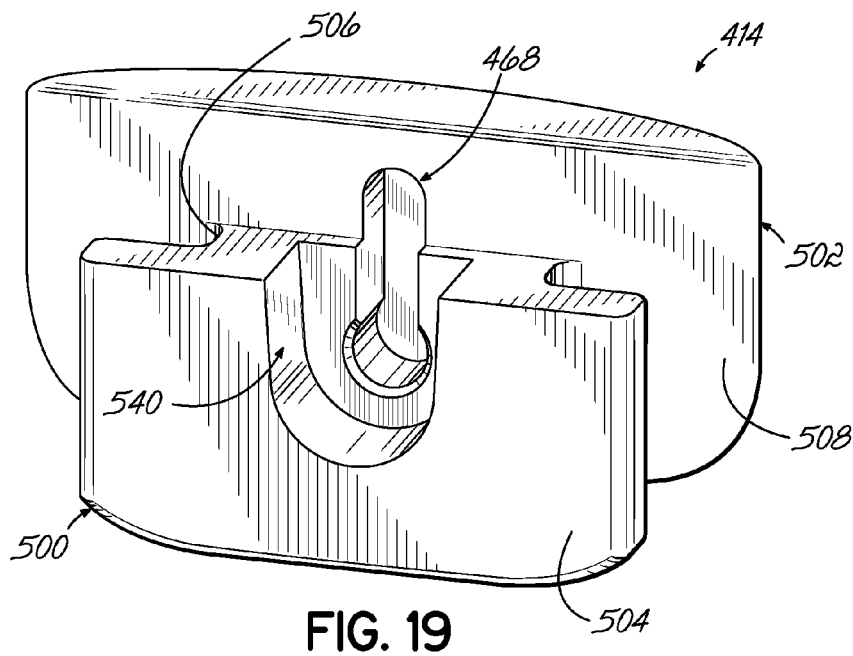
FIG. 19 is a rear perspective view of the ligating slide shown in FIG. 16.

Instead, and as shown in FIGS. 17 and 19, the ligating slide 414 has an engagement portion 500 for engaging the bracket body 412 and an outer contoured portion 502 that forms a significant portion of the labial side 430 of the orthodontic bracket 410. The engagement portion 500 has a T-shaped configuration defining a head 504 having a mesial-distal cross dimension that is slightly less than a mesial-distal cross dimension of the slide engagement track 446 in bracket body 412 so as to be movable therein. Engagement portion 500 further includes a neck 506 that has a mesial-distal cross dimension less than the mesial-distal cross dimension of head 504 and is slightly less than the mesial-distal spacing between the guides 442, 444 so as to be movable therein.

As best shown in FIG. 17, the contoured portion 502 has a mesial-distal cross dimension larger than that of neck 506 and which extends substantially from the mesial side 426 to the distal side 428 of bracket body 412. A lingual side 508 of contoured portion 502 overlies the guides 442, 444 so that the guides 442, 444 are not visible as viewed from the labial side 430 of bracket 410 (FIG. 16). Contoured portion 502 further includes labial side 476 that is generally smooth and contoured, which is in contrast to the irregular configuration of conventional brackets. In this regard, the labial side 476 may be generally arcuate and characterized by a relatively large radius of curvature. For example, the relatively large radius of curvature may be directed to the mesial-distal curvature and/or the occlusal-gingival curvature.

In one embodiment, for example, the radius of curvature for a substantial portion of labial side 476 in the mesial-distal direction may have a single value from mesial side 426 to distal side 428 (e.g., forms a portion of a circle). In this embodiment, the radius of curvature may range between approximately 0.125 inches and approximately 0.375 inches. For example, the radius of curvature may be approximately 0.200 inches. Those of ordinary skill in the art will recognize that the radius of curvature in the mesial-distal direction may include a plurality of discrete values, with each value being relatively large, such as in the range provided above.

Figure 20:
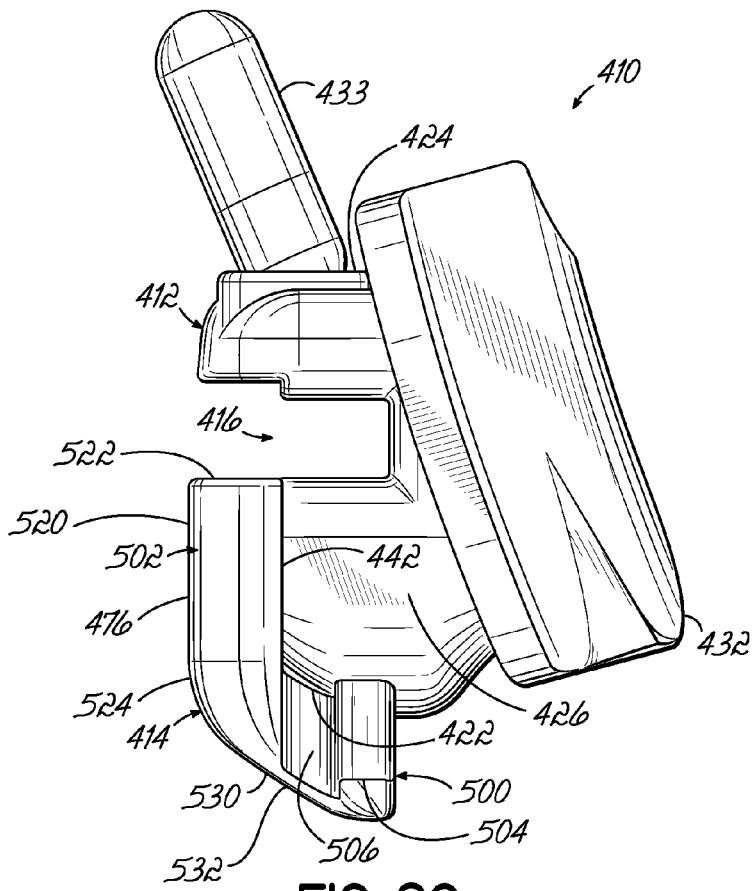
FIG. 20 is a side elevation view of the self-ligating orthodontic bracket shown in FIG. 16.

The radius of curvature in the gingival-occlusal direction may also include one or more values. As shown in FIG. 20, for example, in the gingival-occlusal direction, the labial side 476 may include generally flat portion 520 (e.g., very large radius of curvature) adjacent the gingival edge 522 and a transition portion 524 having a radius of curvature of between approximately 0.020 inches and approximately 0.075 inches. Those of ordinary skill in the art will recognize that the generally flat portion (in view of FIG. 20) may alternatively be formed as a curved or arcuate surface having a radius of curvature as provided above for the mesial-distal direction, for example.

Thus, the primary labial surface as well as the transitions (if any) from the mesial and distal sides 426, 428 and/or the occlusal and gingival side 422, 424 of the bracket 410 to the labial side 430 of the bracket 410 are not sharp or irregular, but are smooth and gradual. Such a configuration eliminates or reduces the sources of discomfort to the patient when oral tissue contacts the bracket 410, and further facilitates movement of soft oral tissue over the bracket 410 resulting in an overall improvement to the comfort of the orthodontic bracket 410.

Brackets on the upper teeth, and especially brackets on the upper molars, tend to have relatively large occlusal sides or faces due to high negative torque typically required by such brackets. Additionally, in conventional brackets, these large occlusal sides tend to be oriented so as to be substantially parallel to the occlusal plane of the teeth. Accordingly, the large occlusal sides and their typical orientation result in increased imposed mastication forces that tend to reduce bond reliability between the bracket and the tooth. However, in a further aspect in accordance with this embodiment, the occlusal side 422 of the orthodontic bracket 410 may be contoured or profiled so as to reduce the likelihood of bond failure.

In this regard, and as best illustrated in FIGS. 16 and 20, in one embodiment, the occlusal side 530 of ligating slide 414 may include a generally flat portion 532 (e.g., a very large radius of curvature) which transitions smoothly with the labial side 476 of the ligating slide 414, such as at transition portion 524 described above. In contrast to conventional brackets, the occlusal side 530 may be angled or sloped generally in the gingival direction and relative to the occlusal plane of the teeth (not shown). Additionally, the occlusal side 422 of the bracket body 412 (e.g., the occlusal sides of guides 442, 444) may also be sloped or contoured in the gingival direction so that the ligating slide 414 and bracket body 412 are relatively flush or smooth along occlusal side 422 when the ligating slide 414 is in the closed position.

Thus, when food or other material in the oral cavity contacts the occlusal side 422 of the orthodontic bracket 410, such as during chewing, the food or material may be deflected in the labial direction. Consequently, the forces imposed on the bracket 410 are reduced and the reliability of the bond between the bracket 410 and the tooth is increased. Although the occlusal side 530 of slide 414 has been described as having generally flat portion 532, this portion may also be curved in one or both of the mesial-distal direction or the gingival-occlusal direction.

In addition to the improvements to the labial side 430 and occlusal side 422 of the bracket 410 as discussed above, the orthodontic bracket 410 may incorporate other features as disclosed in the previous embodiments. By way of example, the bracket 410 may incorporate one of the securing mechanisms described above, the torque indicia, the horizontal slot, the tool receptacle, the chamfer or radiused feature at the end of the ligating slide, the matching system between ligating slide and bracket body, and/or other features described more fully above.

Figure 18:
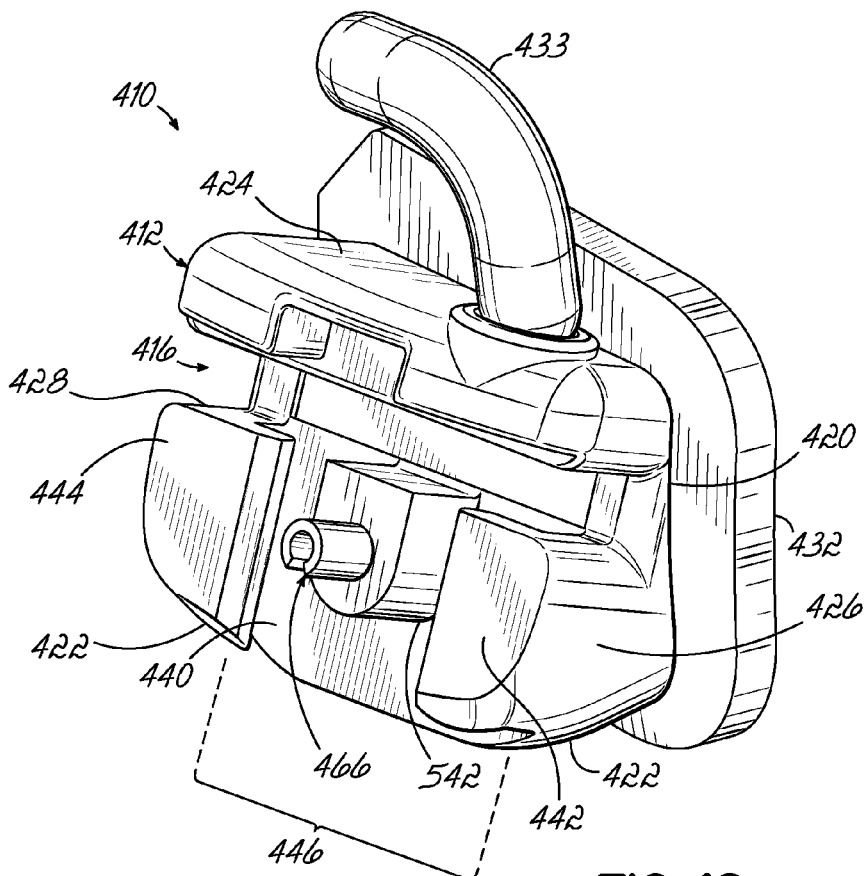
FIG. 18 is a perspective view of the self-ligating orthodontic bracket shown in FIG. 16 with the ligating slide removed from the bracket body.

For instance, as shown in FIGS. 18 and 19, the orthodontic bracket 410 may include a securing mechanism including a spring pin 466 associated with bracket body 412 and a retaining slot 468 formed in the ligating slide 414. Due to size constraints and other design considerations, the retaining slot 468 may be formed in the lingual side 508 of the contoured portion 502 of ligating slide 414. Because the retaining slot 468 extends into the engagement portion 500 (FIG. 19), the engagement portion 500 includes a U-shaped cutout 540 thereby allowing the spring pin 466 to access the retaining slot 468.

In addition, to prevent the spring pin 466 from bending or flexing longitudinally, or laterally (due to the increased distance between the support surface 440 and the retaining slot 468), the bracket body 412 may include a boss or pin support 542 that extends labially from the support surface 440. The pin support 542 has a shape corresponding to cutout 540 and is received in the U-shaped cutout 540 as the ligating slide 414 is moved between the opened and closed positions. The spring pin 466 and retaining slot 468 operate in basically the same manner described above to secure the ligating slide 414 in at least the closed position. Additionally, the spring pin 466 and retaining slot 468 may prevent the ligating slide 414 from disengaging from the bracket body 412, as described more fully above.

Figure 21:
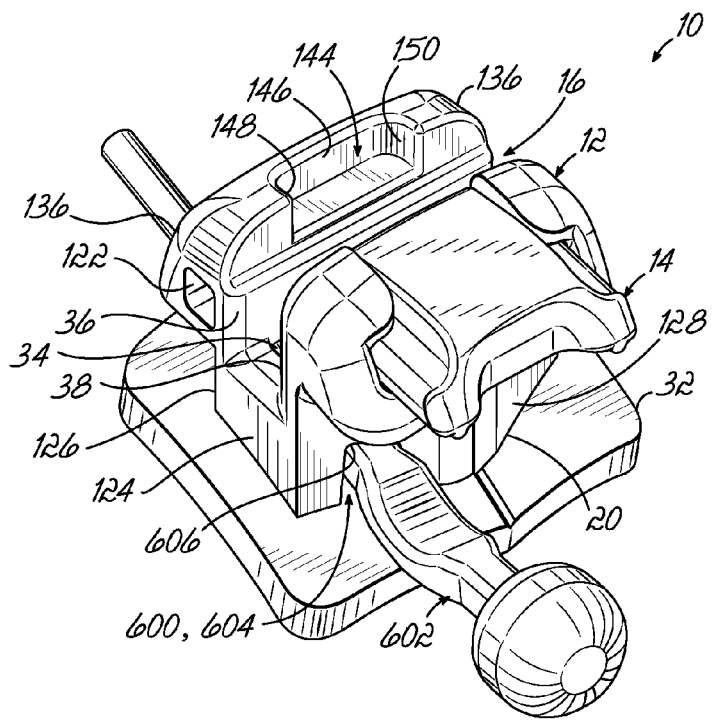
FIG. 21 is a perspective view of a self-ligating orthodontic bracket in accordance with another embodiment of the invention.

With reference to FIG. 21, the orthodontic bracket 10 shown in FIGS. 1-3 may include another feature that improves the use and functionality of the bracket. As discussed earlier, bracket 10 includes a horizontally-oriented slot 122 (e.g., directed generally in the mesial-distal direction) for securing various orthodontic devices. In some applications, it may be desirable to provide additional attachment points to the bracket or attachment points in different orientations. Thus, in addition to the horizontal slot 122, or instead of slot 122, the orthodontic bracket 10 may include a vertical slot 600 (e.g., directed generally in the gingival-occlusal direction). The vertical slot 600 may be configured, for example, to receive a variety of temporary attachment devices, such as, for example, removable hook 602, as illustrated in FIG. 21. Those of ordinary skill in the art will recognize other permanent or temporary orthodontic devices that may be used with vertical slot 600 to effectuate orthodontic treatment.

Horizontal and vertical slots 122, 600 may be configured so as not to interfere with each other when both are utilized on orthodontic bracket 10. Thus, while the horizontal slot 122 may be disposed adjacent tie wings 136, in one embodiment, the vertical slot 600 may be disposed in projecting portion 124. More particularly, projecting portion 124 includes a generally gingival-occlusal directed passage 604 having a first opening (not shown) in the occlusal side 126 of projecting portion 124 and a second opening 606 in the gingival side 128 of projecting portion 124. Furthermore, while the passage 604 may be embedded completely in the material of projecting portion 124, in the exemplary embodiment shown, vertical slot 600 may be disposed adjacent the lingual side 20 of the bracket body 12 such that passage 604 is at least partially defined or bounded by pad 32. Those of ordinary skill in the art will appreciate that vertical slot 600 may instead be disposed in other portions of the bracket body 12 and/or not necessarily be defined by any portion of the pad 32. Furthermore, those of ordinary skill in the art will appreciate that additional slots may be formed in orthodontic bracket 10. For example, additional vertical slots (not shown) may be formed in projecting portion 124.

Orthodontic treatment of teeth may be enhanced by properly locating the brackets on the surface of the teeth. For example, properly locating the brackets on the teeth in the gingival-occlusal direction is desirable. This may be done, for example, by using a fixed reference point on the tooth and basing various measurements to ensure proper positioning of a bracket from this fixed reference point. In some techniques, for example, the occlusal edge of the tooth is used as the fixed reference point. Conventionally, a tool is used to position the brackets on the teeth relative to the fixed reference point. The tool is typically a separate component supplied to the orthodontist independent of the orthodontic brackets. Thus, the orthodontist must, in some fashion, and in the office environment, couple the bracket to the tool so as to properly position the bracket on the surface of the tooth. This type of field assembly process can be difficult, frustrating, tedious, and time consuming.

Figure 23:
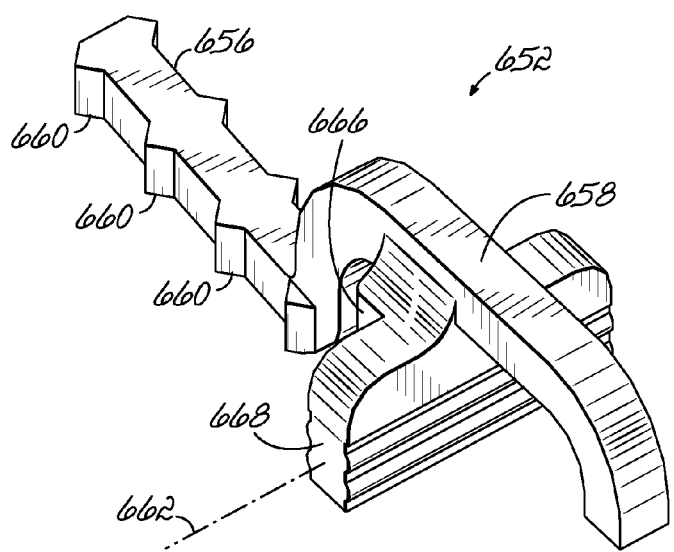
FIG. 23 is a perspective view of the alignment device shown in FIG. 22.
Figure 22:
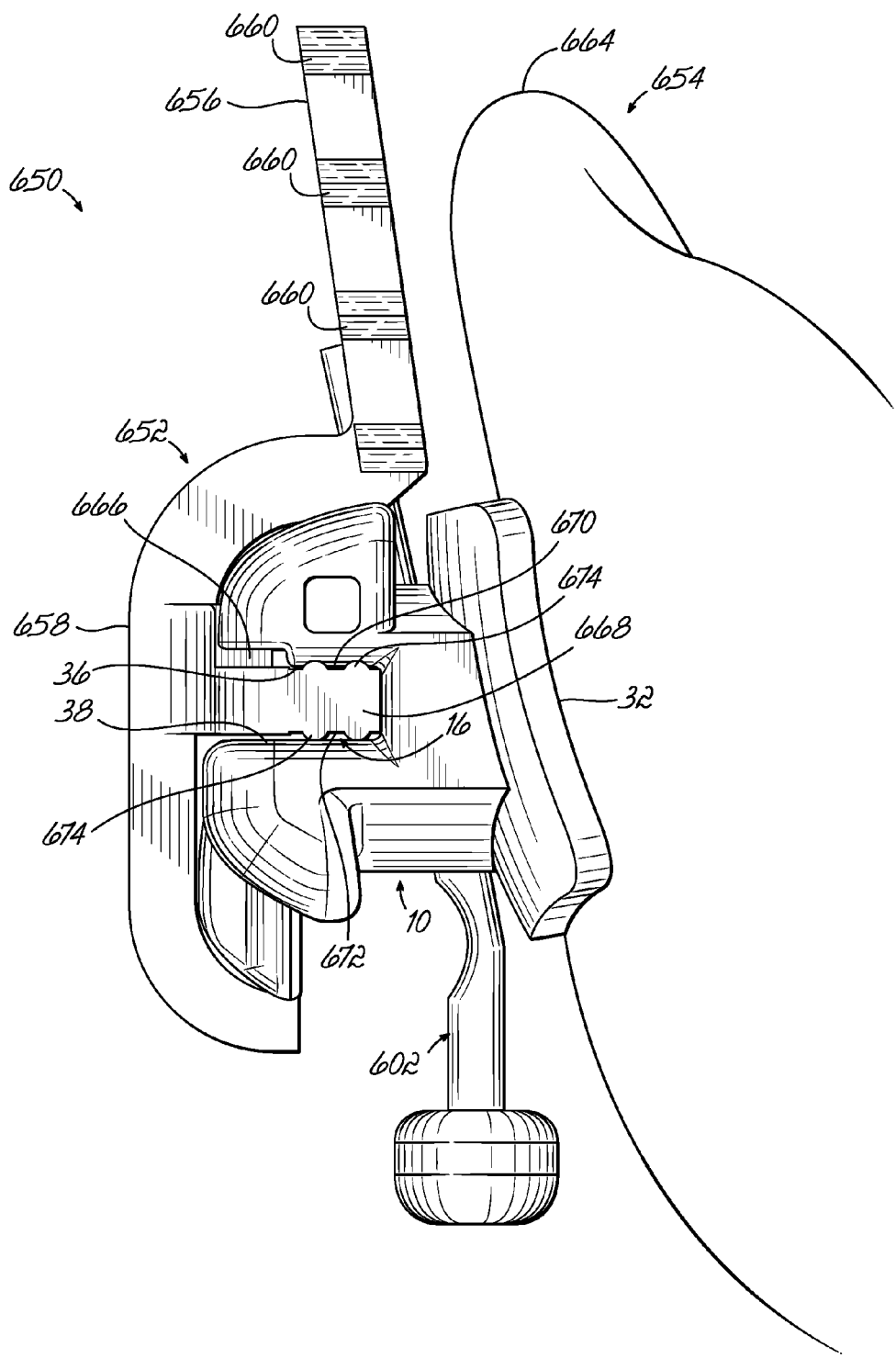
FIG. 22 is a side elevation view of an orthodontic assembly including a self-ligating bracket and an alignment device in accordance with an embodiment of the invention.

Another aspect in accordance with embodiments of the invention addresses such shortcomings in convention methodologies. With reference to FIGS. 22 and 23, in which like reference numerals refer to like features in FIGS. 1-3, an orthodontic assembly 650 includes an alignment device 652 coupled to a self-ligating orthodontic bracket 10 to facilitate deployment and installation thereof onto a tooth 654. The assembly 650 may, for example, be pre-packaged and provided to the orthodontist in a coupled or assembled condition (as shown). Thus, an orthodontist no longer has to perform the field assembly of the bracket to a tool that facilitates proper positioning of the bracket on the tooth. In addition, the alignment device 652 may be designed so as to be disposable. Accordingly, after the bracket 10 has been properly positioned on the tooth, the alignment device 652 may be separated from the bracket 10 and simply discarded. In this regard, it is contemplated that the alignment device 652 may be formed in a cost-effective manner that makes its disposal feasible.

Referring to FIG. 23, alignment device 652 includes an elongate handle portion 656 and a bracket coupling portion 658 offset from and extending from the handle portion 656. Handle portion 656 facilitates deployment of the bracket 10 onto a tooth 654 by providing a gripping portion that an orthodontist may utilize to grasp the assembly 650 and deploy the bracket 10 into a patient's mouth and onto tooth 654. Additionally, handle portion 656 facilitates positioning of the bracket 10 in the occlusal-gingival direction relative to tooth 654. More particularly, handle portion 656 includes one or more marking elements, for example, in the form of ribs 660, which allow the user to precisely place the bracket 10 in a desired occlusal-gingival position on the tooth 654. The exemplary ribs 660 are spaced from one another by predetermined distances (e.g., 1 mm) and each is also spaced from a central axis 662 of the archwire slot 16 by a predetermined distance. Accordingly, a user may, for example, place the bracket 10 in an occlusal-gingival position such that one of the ribs 660 is in alignment with the occlusal edge 664 of tooth 654. This positioning, in turn, gives the user certainty as to the occlusal-gingival position of the bracket 10 relative to the tooth 654.

With particular reference to FIG. 22, the design of handle portion 656 and, more particularly, the position thereof relative to bracket coupling portion 658, facilitates the positioning described above. More specifically, the handle portion 656 is designed such that, when bracket coupling portion 658 is coupled to a bracket 10 having a bonding surface and the bonding surface engages the surface of the tooth 654, handle portion 656 also lies adjacent the surface of tooth 654. For example, the offset relationship between the handle portion 656 and bracket coupling portion 658 facilitates positioning of handle portion 656 adjacent tooth 654 during use. This configuration allows the user to more precisely ascertain the position of the ribs 660 relative to the tooth 654. In this regard, the design of handle portion 656 facilitates the reduction or prevention of parallax errors during deployment of orthodontic bracket 10 onto tooth 654, especially, for example, in the rear of the oral cavity.

With continued reference to the exemplary embodiment of FIGS. 22 and 23, the alignment device 652 may be configured for secured coupling with the bracket 10. For example, the alignment device 652 may be configured to prevent or reduce relative movement between the bracket 10 and alignment device 652 in the mesial-distal direction. In this regard, the alignment device 652 may include a first coupling feature that cooperates with a second coupling feature on the bracket 10 to prevent relative movement in the mesial-distal direction. In one embodiment, the first coupling feature may include a tab 666 and the second coupling feature may include a recess, such as, for example, the tool receptacle 144 (FIG. 21). When the alignment device 652 is coupled to orthodontic bracket 10, the tab 666 fits tightly within the tool receptacle 144 of the bracket 10. Accordingly, the mesial and distal walls 148, 150 of tool receptacle 144 may abut exposed surfaces of tab 666 to limit or restrict mesial-distal movement of the alignment device 652 relative to orthodontic bracket 10. This type of coupling permits deployment of the bracket 10 onto the tooth 654 without a concern for mesial-distal shifting of the alignment device 652 and bracket 10 relative to one another. Moreover, the coupling of tab 666 of the alignment device 652 with tool receptacle 144 permits coupling of device 652 with bracket 10 in only one orientation and position, which may be desirable, for example, during assembly of orthodontic assembly 650.

The alignment device 652 may be further configured to prevent or reduce relative movement between the bracket 10 and alignment device 652 in the gingival-occlusal direction. In this regard, the bracket coupling portion 658 includes a leg 668 that extends for at least a portion of the length of the archwire slot 16 and fits tightly therein to facilitate frictional engagement of bracket 10 with alignment device 652. Leg 668 includes an occlusal surface 670 that abuts slot surface 36 of archwire slot 16, and a gingival surface 672 that abuts the opposed slot surface 38 of archwire slot 16. Additionally, the gingival and occlusal surfaces 670, 672 may include ribs 674 for enhancing the frictional engagement of these surfaces with slot surfaces 36, 38 respectively, of archwire slot 16. The interaction between the leg 668 and archwire slot 16 limits or restricts gingival-occlusal movement of the alignment device 652 relative to orthodontic bracket 10. Thus, the bracket 10 may be deployed on the tooth 654 without a concern for gingival-occlusal shifting of the alignment device 652 and bracket 10 relative to one another.

In one embodiment, the alignment device 652 may be formed from a suitable plastic material and through, for example, a molding process. In one embodiment, the alignment device may be molded from polymers, including, for example, polypropylene. Those of ordinary skill in the art will recognize other suitable materials for forming alignment device 652, as well as other suitable processes for forming the alignment device 652. The material may be selected such that at least leg 668 is somewhat deformable or compressible. In this way, for example, leg 668 may be slightly deformed or compressed when in archwire slot 16 to facilitate the coupling between alignment device 652 and bracket 10. Additionally, in one embodiment, the alignment device 652 may have visual features that permit a user or manufacturer to identify a unique type of bracket 10 to which device 652 may be coupled. For example, and without limitation, either portions or the entirety of alignment device 652 may have a color that corresponds to a specific type of bracket 10. Alternatively, the alignment device 652 may include indicia (e.g., alphanumeric, symbolic, etc.) that match indicia on the orthodontic bracket 10.

Figure 24:
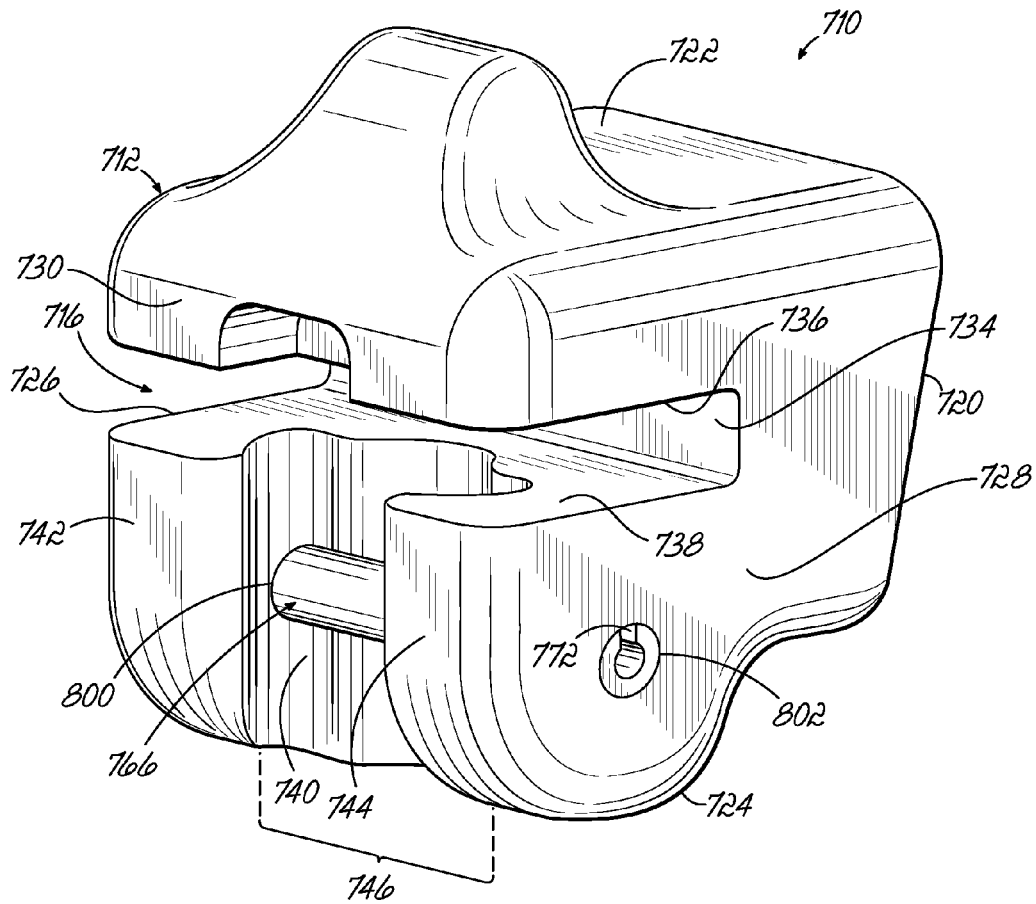
FIG. 24 is a perspective view of a self-ligating orthodontic bracket in accordance with another embodiment of the invention with the ligating slide removed from the bracket body.
Figure 25:
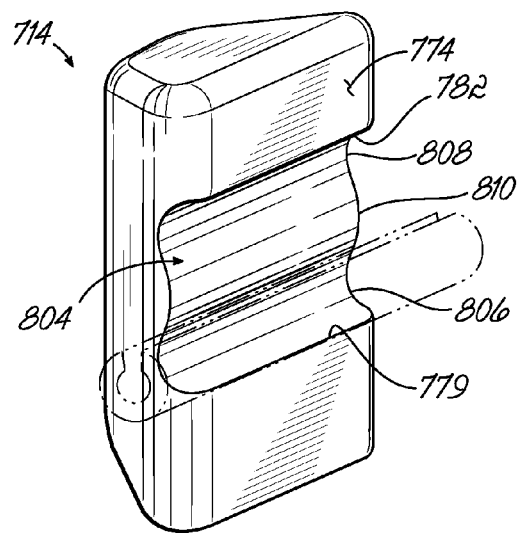
FIG. 25 is a perspective view of a ligating slide used with the orthodontic bracket shown in FIG. 24.

In the various embodiments including spring pin 66 as part of the securing mechanism described above, the spring pin 66 was oriented generally perpendicular to the archwire slot 16. Thus, for example, the spring pin 66 generally projected in the labial-lingual direction. Aspects of the invention are not so limited as other orientations of spring pin 66 are possible. For example, the spring pin 66 may be oriented in a direction that is generally parallel to the archwire slot 16. FIGS. 24 and 25, in which features similar to that shown in FIGS. 1-4 have similar reference numerals but are preceded by the number 7, illustrate a self-ligating bracket 710 having a spring pin 766 oriented in a generally mesial-distal direction.

In this regard, orthodontic bracket 710 includes a bracket body 712 including a pair of guides 742, 744 that overlie in spaced relation a support surface 740 that defines a slide engagement track 746 for receiving a ligating slide 714. Each of the guides 742, 744 includes a bore 800, 802, respectively, that receives a portion of spring pin 766 therein such that the spring pin 766 is generally parallel to the archwire slot 716 and extends across the slide engagement track 746. While the embodiment shown in FIG. 24 shows the spring pin 766 extending into both guides 742, 744, it should be recognized that in alternative embodiments, the spring pin 766 may extend from only one of the guides 742, 744. At least one of the bores 800, 802 may be open at the mesial or distal sides 726, 728 for inserting the spring pin 766 within bores 800, 802 during assembly.

As shown in FIG. 25, a retaining slot 804 may be formed in the lingual side 774 of the ligating slide 714 and extends generally in the gingival-occlusal direction. In one embodiment, the retaining slot 804 also extends across the mesial-distal extent of the ligating slide 714. In alternative embodiments, however, the retaining slot 804 may extend for a portion of the mesial-distal extent of ligating slide 714. The retaining slot 804 is shaped in the gingival-occlusal direction so as to cooperate with spring pin 766 and secure the ligating slide 714 in at least the closed position relative to bracket body 714. In this regard, retaining slot 804 includes a first arcuately shaped recess 806 adjacent the gingival end 779, and a second arcuately shaped recess 808 adjacent the occlusal end 782. Intermediate the first and second arcuately shaped recesses 806, 808 is a raised ridge portion 810.

In operation, when the ligating slide 714 is in the closed position, the spring pin 766 (e.g., a lateral surface thereof) is disposed in the first arcuately shaped recess 806 of retaining slot 804 and is permitted to radially expand such that the spring pin 766 engages the wall of recess 806. Those of ordinary skill in the art will recognize that the spring pin 766 does not have to engage the wall of first arcuately shaped recess 806, but must at least have a cross dimension when radially expanded such that the spring pin 766 engages the ridge portion 810 as the ligating slide 714 is moved toward the opened position. When so disposed in the first arcuately shaped recess 806, the raised ridge 810 provides a threshold level of resistance to any movement of the ligating slide 714 away from the closed position and toward the opened position. However, if a sufficiently large opening force is applied to ligating slide 714 in, for example, the gingival direction, the interaction between the retaining slot 804 and spring pin 766 causes the pin 766 to radially contract (due to squeezing imposed by raised ridge 810) so that spring pin 766 moves along raised ridge 810.

Once positioned on the raised ridge 810, the spring pin 766 bears against a lingual surface thereof such that a threshold sliding force, which is less than, and perhaps significantly less than the opening force, must be imposed to overcome the drag and move the ligating slide 714 relative to the bracket body 712 as spring pin 766 traverses raised ridge 810. Thus, once opened, the ligating slide 714 does not just freely slide or drop to the fully opened position, but must be purposefully moved toward the opened position. If the ligating slide 714 is only partially opened, the slide 714 may be configured to maintain its position relative to the bracket body 712 (due to the friction forces) until the threshold sliding force is imposed to continue moving the slide 714 toward the opened position. When the ligating slide 714 is moved toward the closed position, the spring pin 766 recovers or snaps back to its radially expanded position as the spring pin 766 enters the first arcuately shaped recess 806 to once again secure the ligating slide 714 in the closed position.

The amount of force required to overcome the threshold sliding force as the spring pin 766 moves relative to the raised ridge portion 810 may vary during movement between the opened and closed positions of ligating slide 714. In one embodiment, for example, the raised ridge portion 810 may have a height that slightly tapers so as to increase in the direction of the occlusal end 782 of the retaining slot 804 (not shown). Accordingly, the sliding force required for relative movement between the spring pin 766 and the retaining slot 804 of ligating slide 714 decreases as the ligating slide 714 is moved toward the opened position and increases as the ligating slide 714 is moved toward the closed position. Those of ordinary skill in the art may recognize other ways to vary the sliding force of the ligating slide 714 as the slide is moved between the opened and closed positions.

Similar to FIG. 5, the embodiment shown in FIG. 25 includes second arcuately shaped recess 808 adjacent the occlusal end 782. Thus, the ligating slide 714 may be secured in the opened position so as to require a sufficiently high closing force to initiate movement of the ligating slide 714 away from the opened position and toward the closed position. In this regard, when the ligating slide 714 is in the closed position, the spring pin 766 is disposed in the first arcuately shaped recess 806 and a sufficiently large opening force must be applied to the ligating slide 714 in the gingival direction to contract spring pin 766 and allow the pin 766 to move onto raised ridge portion 810. As the ligating slide 714 is moved further toward the opened position, the spring pin 766 snaps back to its radially expanded position as the spring pin 766 enters second arcuately shaped recess 808 at the occlusal end 782 of the retaining slot 804. When so disposed therein, the raised ridge portion 810 provides a threshold level of resistance to any movement of the ligating slide 714 away from the opened position and toward the closed position. Only after a sufficiently large closing force is applied to the ligating slide 714 in the occlusal direction, will the spring pin 766 radially contract so that the spring pin 766 moves onto the raised ridge portion 810 of the retaining slot 804.

Figure 26:
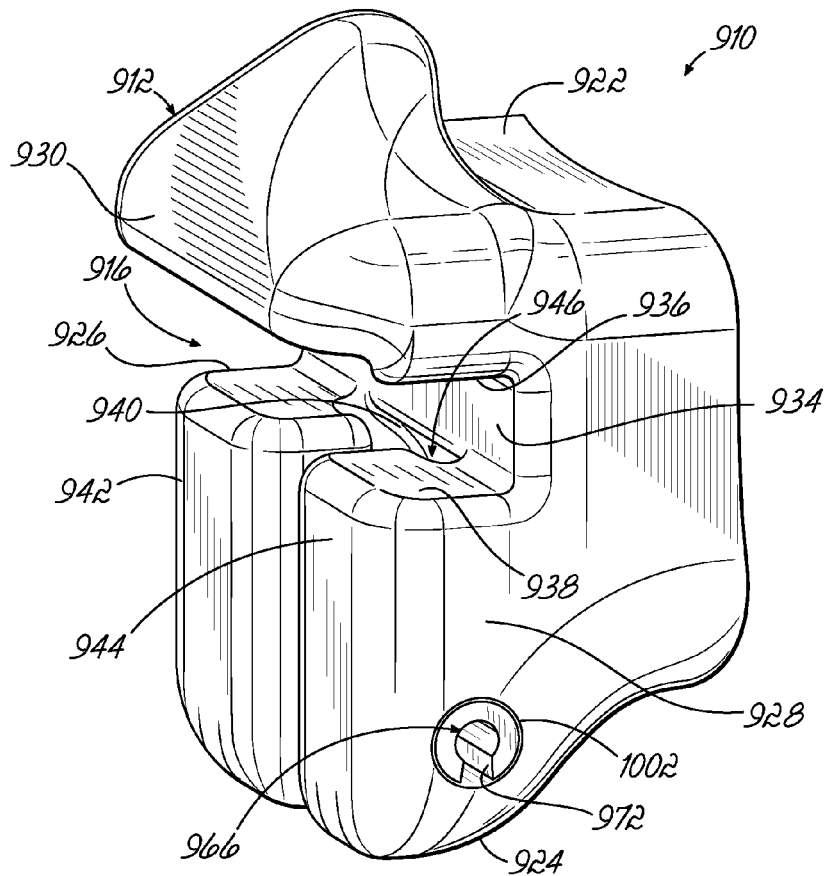
FIG. 26 is a perspective view of a self-ligating orthodontic bracket in accordance with another embodiment of the invention with the ligating slide removed from the bracket body.
Figure 27:
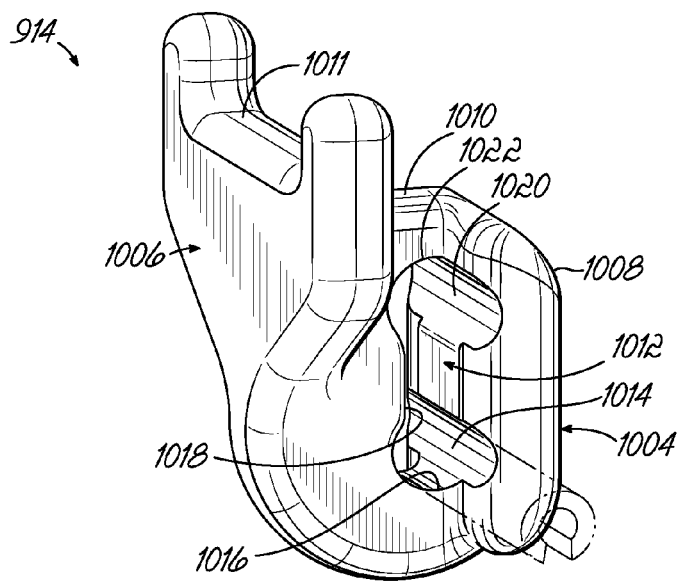
FIG. 27 is a perspective view of a ligating slide used with the orthodontic bracket shown in FIG. 26.

Another embodiment having the spring pin oriented so as to be generally parallel to the archwire slot is shown in FIGS. 26 and 27, in which features similar to that shown in FIGS. 1-4 have similar reference numerals but are preceded by the number 9. In this regard, orthodontic bracket 910 includes a bracket body 912 including a pair of guides 942, 944 that overlie in spaced relation to a support surface 940 that defines a slide engagement track 946 for receiving a ligating slide 914. Each of the guides 942, 944 includes a bore 1002 (one shown) that receives a portion of spring pin 966 therein such that the spring pin 966 is generally parallel to the archwire slot 916 and extends across the slide engagement track 946. While the embodiment shown in FIG. 25 shows the spring pin 966 extending into both guides 942, 944, it should be recognized that in alternative embodiments, the spring pin 966 may extend from only one of the guides 942, 944. At least one of the bores in guides 942, 944 may be open at the mesial or distal sides 926, 928 for inserting the spring pin 966 therein during assembly.

As shown in FIG. 27, and similar to the ligating slide shown in FIGS. 16-20, the ligating slide 914 includes an engagement portion 1004 for engaging bracket body 912 and an outer portion 1006 that forms a portion of the labial side 930 of the orthodontic bracket 910. The engagement portion 1004 has a T-shaped configuration defining a head 1008 having a mesial-distal cross dimension that is slightly less than a mesial-distal cross dimension of the slide engagement track 946 in bracket body 912 so as to be movable therein. Engagement portion 1004 further includes a neck 1010 that has a mesial-distal cross dimension less than the mesial-distal cross dimension of head 1008 and is slightly less than the mesial-distal spacing between the guides 942, 944 so as to be movable therein. Additionally, the outer portion 1006 has a Y-shaped configuration configured to cover a substantial portion of the archwire slot 916 in the mesial-distal direction as well as to define a tool receptacle 1011 for receiving a tool and opening the ligating slide 914 in accordance with that discussed above.

A retaining slot 1012 is formed in the ligating slide 914 and extends generally in the gingival-occlusal direction. The retaining slot 1012 may be positioned at least in the neck 1010 of engagement portion 1004 and may be formed as a through slot, e.g., extending from the mesial side of the neck 1010 to the distal side of the neck 1010. Those of ordinary skill in the art will recognize that the retaining slot 1012 may also be formed in the neck 1010 as a blind slot. The retaining slot 1012 is shaped so as to cooperate with spring pin 966 and secure the ligating slide 914 in at least the closed position relative to bracket body 912. In this regard, retaining slot 1012 includes a first enlarged portion 1014 adjacent the gingival end 1016 of retaining slot 1012 in communication with a straight segment portion 1018 similar to that shown in FIG. 4B. The retaining slot 1012 may further include a second enlarged portion 1020 adjacent an occlusal end 1022, similar to that shown in FIG. 5.

In operation, when the ligating slide 914 is in the closed position, the spring pin 966 (e.g., a lateral surface thereof) is disposed in the first enlarged portion 1014 of retaining slot 1012 and is permitted to radially expand such that the spring pin 966 engages the wall of enlarged portion 1014. Those of ordinary skill in the art will recognize that the spring pin 966 does not have to engage the wall of first enlarged portion 1014, but must at least have a cross dimension when radially expanded that is larger than the cross dimension of the straight segment portion 1018. When so disposed in the first enlarged portion 1014, the protrusions at the transition between the first enlarged portion 1014 and straight segment portion 1018 provide a threshold level of resistance to any movement of the ligating slide 914 away from the closed position and toward the opened position. However, if a sufficiently large opening force is applied to ligating slide 914 in, for example, the gingival direction, the interaction between the retaining slot 1012 and spring pin 966 causes the pin 966 to radially contract (due to squeezing imposed by the slot) so that spring pin 966 moves past the protrusions and into the straight segment portion 1018.

Once positioned in the straight segment portion 1018, the spring pin 966 bears against the walls thereof such that a threshold sliding force, which is less than, and perhaps significantly less than the opening force, must be imposed to overcome the drag and move the ligating slide 914 relative to the bracket body 912 as spring pin 966 traverses straight segment portion 1018. Thus, once opened, the ligating slide 914 does not just freely slide or drop to the fully opened position, but must be purposefully moved toward the opened position. If the ligating slide 914 is only partially opened, the slide 914 may be configured to maintain its position relative to the bracket body 912 (due to the friction forces) until the threshold sliding force is imposed to continue moving the slide 914 toward the opened position. When the ligating slide 914 is moved toward the closed position, the spring pin 966 recovers or snaps back to its radially expanded position as the spring pin 966 enters the enlarged portion 1014 to once again secure the ligating slide 914 in the closed position.

The amount of force required to overcome the threshold sliding force as the spring pin 966 moves relative to the straight segment portion 1018 may vary during movement between the opened and closed positions of ligating slide 914, such as by varying the cross dimension of straight segment portion 1018. Those of ordinary skill in the art may recognize other ways to vary the sliding force of the ligating slide 914 as the slide is moved between the opened and closed positions.

Similar to FIG. 5, the embodiment shown in FIG. 27 includes second enlarged portion 1020 adjacent the occlusal end 1022. Thus, the ligating slide 914 may be secured in the opened position so as to require a sufficiently high closing force to initiate movement of the ligating slide 914 away from the opened position and toward the closed position. In this regard, when the ligating slide 914 is in the closed position, the spring pin 966 is disposed in the first enlarged portion 1012 and a sufficiently large opening force must be applied to the ligating slide 914 in the gingival direction to contract spring pin 966 and allow pin 966 to move into straight segment portion 1018. As the ligating slide 914 is moved further toward the opened position, the spring pin 966 snaps back to its radially expanded position as the spring pin 966 enters second enlarged portion 1020 at the occlusal end 1022 of the retaining slot 1012. When so disposed therein, the protrusions at the transition between the second enlarged portion 1020 and straight segment portion 1018 provide a threshold level of resistance to any movement of the ligating slide 914 away from the opened position and toward the closed position. Only after a sufficiently large closing force is applied to the ligating slide 914 in, for example, the occlusal direction, will the spring pin 966 radially contract so that the spring pin 966 moves into straight segment portion 1018 of the retaining slot 1012.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in any combinations depending on the needs and preferences of the user.

What is claimed is:

1. An orthodontic bracket for coupling an archwire with a tooth, comprising:
   a bracket body configured to be mounted to the tooth, the bracket body including an archwire slot adapted to receive the archwire therein;
   a movable member engaged with the bracket body and movable relative thereto between an opened position in which the archwire is insertable into the archwire slot, and a closed position in which the movable member retains the archwire in the archwire slot; and
   a securing mechanism configured to secure the movable member in at least the closed position, the securing mechanism including a tubular pin in one of the bracket body and the movable member, and a receiving portion in the other of the bracket body and the movable member,
   wherein the pin is capable of expanding and contracting in a generally radial direction relative to a central axis thereof and the pin cooperates with the receiving portion to secure the movable member in at least the closed position; and
   wherein the pin includes a sidewall, an interior space, and a slit formed in the sidewall along at least a portion of the length of the pin that communicates with the interior space, the slit facilitating the radial expansion and contraction of the pin.

2. The orthodontic bracket of claim 1, wherein the slit extends for the entire length of the pin.

3. The orthodontic bracket of claim 1, wherein the pin is associated with the bracket body and the receiving portion is associated with the movable member.

4. The orthodontic bracket of claim 1, wherein the movable member is a ligating slide.

5. The orthodontic bracket of claim 1, wherein the receiving portion includes a retaining slot adapted to receive the pin therein.

6. The orthodontic bracket of claim 5, wherein the retaining slot comprises:
   a first enlarged portion at a first end thereof having a first cross dimension; and
   a straight segment portion communicating with the first enlarged portion and having a second cross dimension less than the first cross dimension to define at least one protrusion at a transition therebetween.

7. The orthodontic bracket of claim 6, further comprising:
   a second enlarged portion at a second end of the retaining slot and communicating with the straight segment portion, the second enlarged portion having a third cross dimension larger than the second cross dimension.

8. The orthodontic bracket of claim 7, wherein the pin has a first shape and the second enlarged portion has a second shape that generally corresponds to the first shape.

9. The orthodontic bracket of claim 8, wherein the first and second shapes are generally circular.

10. The orthodontic bracket of claim 6, wherein the straight segment portion is tapered.

11. The orthodontic bracket of claim 6, wherein the pin has a first shape and the first enlarged portion has a second shape that generally corresponds to the first shape.

12. The orthodontic bracket of claim 11, wherein the first and second shapes are generally circular.

13. The orthodontic bracket of claim 5, wherein the retaining slot includes a blind slot.

14. The orthodontic bracket of claim 5, wherein the retaining slot comprises:
   a first enlarged portion at an end thereof defining a first centerline; and
   a straight segment portion communicating with the first enlarged portion and defining a second centerline that is in alignment with the first centerline.

15. The orthodontic bracket of claim 1, wherein the movable member includes a pushing element adjacent an end thereof and configured to guide the archwire into the archwire slot as the movable member is moved toward the closed position.

16. The orthodontic bracket of claim 15, wherein the pushing element includes a chamfer formed on a leading edge of the movable member.

17. The orthodontic bracket of claim 16, wherein the chamfer is non-uniformly formed on the movable member.

18. The orthodontic bracket of claim 1, wherein the pin is substantially perpendicular to the archwire slot.

19. The orthodontic bracket of claim 1, wherein the pin is substantially parallel to the archwire slot.

20. The orthodontic bracket of claim 1, wherein the securing mechanism is configured to prevent the movable member from disengaging the bracket body.

21. The orthodontic bracket of claim 20, wherein the receiving portion includes a retaining slot having a first end, the pin engaging the first end of the retaining slot when in the opened position to prevent the movable member from disengaging the bracket body.

22. An orthodontic bracket for coupling an archwire with a tooth, comprising:
   a bracket body configured to be mounted to the tooth, the bracket body including an archwire slot adapted to receive the archwire therein;
   a movable member engaged with the bracket body and movable relative thereto between an opened position in which the archwire is insertable into the archwire slot, and a closed position in which the movable member retains the archwire in the archwire slot; and
   a securing mechanism configured to secure the movable member in at least the closed position, the securing mechanism including a tubular pin secured in one of the bracket body and the movable member, and further including a receiving portion in the other of the bracket body and the movable member,
   wherein at least a portion of the pin is capable of moving between an expanded state and a contracted state to thereby define a radial expansion and contraction of the pin relative to a central axis, the pin having a width defining a first cross dimension in the expanded state and a second cross dimension less than the first cross dimension in the contracted state, the pin cooperating with the receiving portion to secure the movable member in at least the closed position;
   wherein the pin includes a sidewall, an interior space, and a slit formed in the sidewall along at least a portion of the length of the pin that communicates with the interior space, the slit facilitating the radial expansion and contraction of the pin.

23. An orthodontic bracket for coupling an archwire with a tooth, comprising:

a bracket body configured to be mounted to the tooth, the bracket body including an archwire slot adapted to receive the archwire therein;

a movable member engaged with the bracket body and movable relative thereto between an opened position in which the archwire is insertable into the archwire slot, and a closed position in which the movable member retains the archwire in the archwire slot; and a securing mechanism configured to secure the movable member in at least the closed position, the securing mechanism including a tubular pin extending from the bracket body, and a receiving portion in the movable member, wherein the pin includes a sidewall, an interior space, and a slit formed in the sidewall along at least a portion of the length of the pin that communicates with the interior space, the slit facilitating the radial expansion and contraction of the pin relative to a central axis thereby cooperating with the receiving portion to secure the movable member in at least the closed position.

\* \* \* \* \*